(12) United States Patent
Hecker et al.

(10) Patent No.: US 8,063,025 B2
(45) Date of Patent: Nov. 22, 2011

(54) NUCLEOSIDE PRODRUGS AND USES THEREOF

(75) Inventors: Scott J. Hecker, Del Mar, CA (US); K. Raja Reddy, San Diego, CA (US); Zhili Sun, San Diego, CA (US); Brett C. Bookser, San Diego, CA (US); David Bernard Smith, San Mateo, CA (US)

(73) Assignee: Metabasis Therapeutics, Inc., La Jolla, CA (US)

( * ) Notice: Subject to any disclaimer, the term of this patent is extended or adjusted under 35 U.S.C. 154(b) by 244 days.

(21) Appl. No.: 12/313,992

(22) Filed: Nov. 26, 2008

(65) Prior Publication Data

US 2009/0209481 A1 Aug. 20, 2009

Related U.S. Application Data

(60) Provisional application No. 60/991,163, filed on Nov. 29, 2007, provisional application No. 61/084,544, filed on Jul. 29, 2008.

(51) Int. Cl.
*A01N 43/04* (2006.01)
*A61K 31/70* (2006.01)
(52) U.S. Cl. ............... 514/48; 514/42; 514/43; 514/45; 514/49; 514/50; 514/51; 514/52
(58) Field of Classification Search ................ None
See application file for complete search history.

(56) References Cited

U.S. PATENT DOCUMENTS

| 2005/0075309 A1 | 4/2005 | Storer et al. |
| 2007/0021388 A1 | 1/2007 | Reddy et al. |

FOREIGN PATENT DOCUMENTS

WO WO 2006/033709 A2 3/2006

OTHER PUBLICATIONS

Supplementary European Search Report issued in EP Appln. 08855731.9 on Feb. 28, 2011.

*Primary Examiner* — Patrick Lewis

(74) *Attorney, Agent, or Firm* — Arnold & Porter LLP

(57) ABSTRACT

Compounds having the formula I or II wherein $R^1$, $R^2$, B, and V are as defined herein are Hepatitis C virus NS5b polymerase inhibitors. Also disclosed are compositions and methods for treating an HCV infection and inhibiting HCV replication.

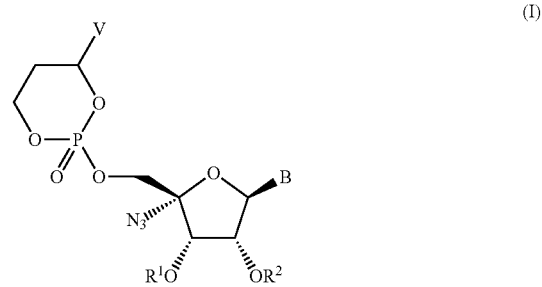

(I)

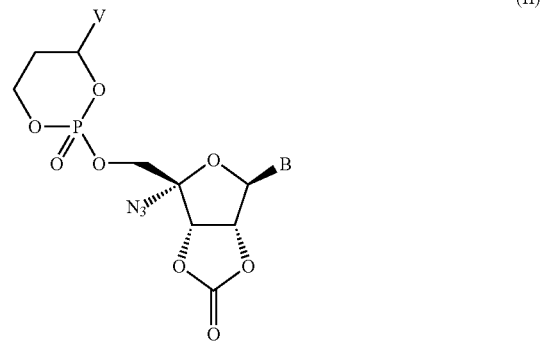

(II)

18 Claims, 1 Drawing Sheet

NUCLEOSIDE PRODRUGS AND USES THEREOF

CROSS REFERENCE TO PRIOR APPLICATIONS

This application claims the benefit of priority to U.S. Ser. No. 60/991,163 filed Nov. 29, 2007 and to U.S. Ser. No. 61/084,544 filed Jul. 29, 2008 both of which are hereby incorporated in their entirety by reference.

FIELD OF THE INVENTION

The present invention relates to nucleoside derivatives which are efficiently absorbed orally and produce high levels of the corresponding phosphorylated nucleoside in the liver. The monophosphates can be converted into the respective triphosphate which inhibit HCV replication and are useful for treating hepatitis C virus (HCV) infection.

BACKGROUND OF THE INVENTION

In recent years there has been much interest in identifying nucleoside inhibitors of the NS5B polymerase for treatment of hepatitis C virus (HCV) infection. While initial reports from researchers in this area described modest efficacy, the tremendous potential of this class of agents became clear when Merck presented the results of evaluation of MK-0608 in the chimpanzee. (Olsen, D. B.; Carroll, S. S.; Davies, M. E.; Handt, L.; Koeplinger, K.; Zhang, R.; Ludmerer, S.; Mac-Coss, M.; Hazuda, D. J. Robust suppression of viral replication in HCV infected chimpanzees by a nucleoside inhibitor of the NS5B polymerase. *Antivir. Ther.* 2006, 11 (5, Suppl.): S7. (15th International HIV Drug Resistance Workshop, Jun. 13-17, 2006; Sitges, Spain.)) In this study, a >5 $\log_{10}$ reduction in viral titer was achieved in 7 days at an intravenous dose of 2 mg/kg/day.

Other agents advanced into development have not achieved such dramatic efficacy. For example, NM283 (Idenix, recently discontinued) achieved only a 1.15 $\log_{10}$ reduction in viral titer in the chimpanzee (7 days, 16.6 mg/kg/day). (Standring D. N.; Lanford R.; Wright T.; Chung R. T.; Bichko V.; Cretton-Scott E.; Pan-Zhou X.; Bergelson S.; Qu L.; Tausek M.; Bridges E.; Moussa A.; Storer R.; Pierra C.; Benzaria S.; Gosselin G.; La Colla P.; Sommadossi J. P. NM 283 has potent antiviral activity against genotype 1 chronic hepatitis C virus (HCV-1) infection in the chimpanzee. *J. Hepatology*, 2003, 38, (Supp 2), 3.) In a phase 2 study, R1626 (Roche) at 1500 mg BID for 14 days achieved a mean reduction in serum viral titer of 1.2 $\log_{10}$. (Roberts, S.; Cooksley, G.; Shaw, D.; Berns, H. K.; Brandl, M. T.; Fettner, S. H.; Hill, G.; Ipe, D.; Klumpp, K.; Mannino, M.; O'Mara, E.; Tu, Y.; Washington, C. B., Interim results of a multiple ascending dose study of R1626, a novel nucleoside analog targeting HCV polymerase in chronic HCV patients. 41$^{st}$ Annual Meeting of the European Association for the Study of the Liver, Vienna, Apr. 26-30, 2006.)

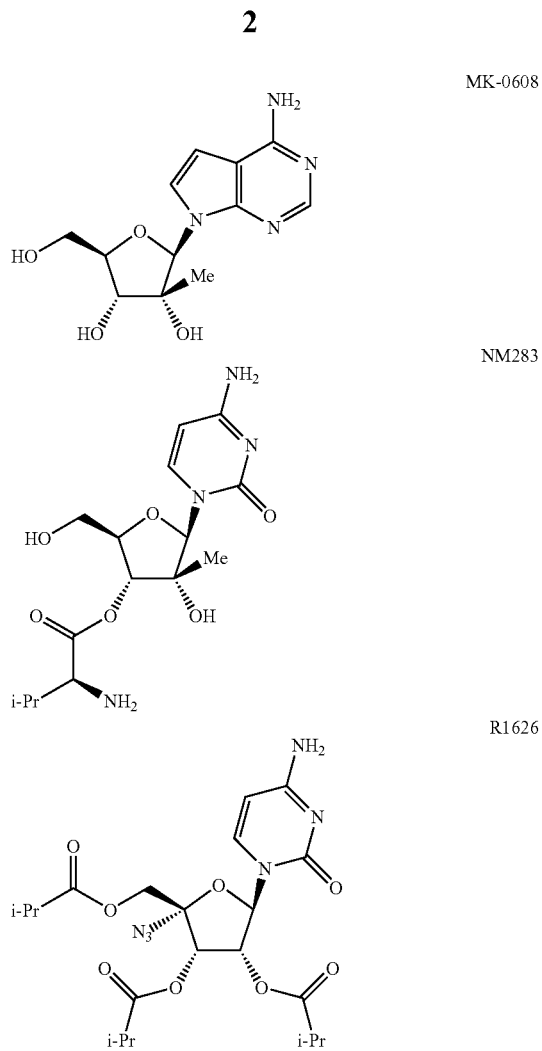

The difference in efficacy between these agents, all of which display good plasma levels of the nucleoside, is likely due to differences in rates of phosphorylation and resulting levels of triphosphate in the liver. One method of circumventing a slow rate of initial nucleoside phorphorylation is to utilize a prodrug of the nucleoside monophosphate (kinase bypass). A number of prodrugs have been explored for this purpose, although few have been shown to achieve oral bioavailability and intracellular delivery of the monophosphate in vivo.

One such class of prodrugs is the aryl amidate (McGuigan) type. While these prodrugs have shown impressive intracellular delivery of monophosphates in vitro, there are few reports of in vivo application. (By contrast, their track record with phosphonates has been better.) One notable report by McGuigan details pharmacokinetic evaluation in the cynomolgus monkey of an aryl amidate prodrug of abacavir. (McGuigan, C.; Harris, S. A.; Daluge, S. M.; Gudmundsson, K. S.; McLean, E. W.; Burnette, T. C.; Marr, H.; Hazen, R.; Condreay, L. D.; Johnson, L.; De Clercq, E.; Balzarini, J. Application of phosphoramidate pronucleotide technology to abacavir leads to a significant enhancement of antiviral potency. *J. Med. Chem.* 2005, 48, 3504-3515) This article reports extremely rapid clearance of the prodrug from plasma when administered i.v. The dearth of other literature reports of in vivo characterization of aryl amidate prodrugs, despite numerous applications citing in vitro characterization, suggests that these prodrugs are not sufficiently stable for successful in vivo application.

An alternative class of monophosphate prodrugs that target the liver are the cyclic 1-aryl-1,3-propanyl ester (HepDirect) prodrugs. (Erion, M. D.; Reddy, K. R.; Boyer, S. H.; Matelich, M. C.; Gomez-Galeno, J.; Lemus, R. H.; Ugarkar, B. G.; Colby, T. J.; Schanzer, J.; Van Poelje, P. D. Design, synthesis, and characterization of a series of cytochrome P(450) 3A-activated prodrugs (HepDirect prodrugs) useful for targeting phosph(on)ate-based drugs to the liver. *J. Am. Chem. Soc.* 2004, 126, 5154-5163; Erion, M. D.; van Poelje, P. D.; Mackenna, D. A.; Colby, T. J.; Montag, A. C.; Fujitaki, J. M.; Linemeyer, D. L.; Bullough, D. A. Liver-targeted drug delivery using HepDirect prodrugs. *J. Pharmacol. Exp. Ther.* 2005, 312, 554-560) One HepDirect phosphate prodrug, MB07133, has been advanced to human clinical trials. (Boyer, S. H.; Sun, Z.; Jiang, H.; Esterbrook, J.; Gomez-Galeno, J. E.; Craigo, W.; Reddy, K. R.; Ugarkar, B. G.; MacKenna, D. A.; Erion, M. D. Synthesis and characterization of a novel liver-targeted prodrug of cytosine-1-β-D-arabinofuranoside monophosphate for the treatment of hepatocellular carcinoma. *J. Med. Chem.* 2006, 49, 7711-7720). MB07133 is a prodrug of cytarabine 5'-O-monophosphate (araCMP).

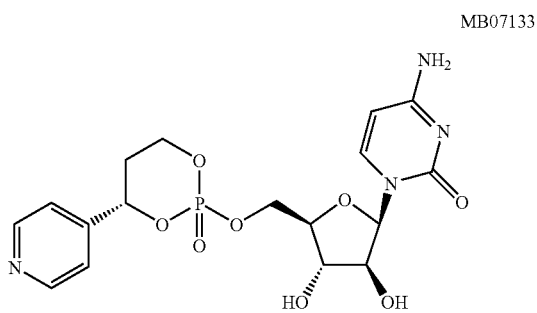

MB07133

Scientists at Roche, in collaboration with McGuigan at Cardiff University, recently reported the synthesis and evaluation of aryl amidate monophosphate prodrugs of 4'-azidouridine. (Perrone, P.; Luoni, G. M.; Kelleher, M. R.; Daverio, F.; Angell, A.; Mulready, S.; Congiatu, C.; Rajyaguru, S.; Martin, J. A.; Leveque, V.; Le Pogam, S.; Najera, I.; Klumpp, K.; Smith, D. B.; McGuigan, C. Application of the phosphoramidate ProTide approach to 4'-azidouridine confers submicromolar potency versus hepatitis C virus on an inactive nucleoside. *J. Med. Chem.* 2007, 50, 1840-1849) Whereas R1479 (the nucleoside parent of R1626) achieves reasonable potency in the cell-based replicon assay, 4'-azidouridine is inactive despite similar potency of its triphosphate as an inhibitor of RdRp. (Smith, D. B.; Martin, J. A.; Klumpp, K.; Baker, S. J.; Blomgren, P. A.; Devos, R.; Granycome, C.; Hang, J.; Hobbs, C. J.; Jiang, W.-R.; Laxton, C.; Le Pogam, S.; Leveque, V.; Ma, H.; Maile, G.; Merrett, J. H.; Pichota, A.; Sarma, K.; Smith, M.; Swallow, S.; Symons, J.; Vesey, D.; Najera, I.; Cammack, N. Design, synthesis and antiviral properties of 4'-substituted ribonucleosides as inhibityors of hepatitis C virus replication: the discovery of R1479. *Bioorg. Med. Chem. Lett.* 2007 17:2570.) Certain aryl amidate monophosphate prodrugs of 4'-azidouridine display replicon activity ($EC_{50}$ as low as 0.22 μM), indicating that the first phosphorylation step is the problematic one. In vivo evaluation of these prodrugs was not reported.

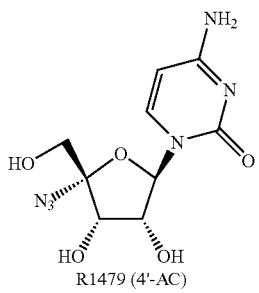

R1479 (4'-AC)

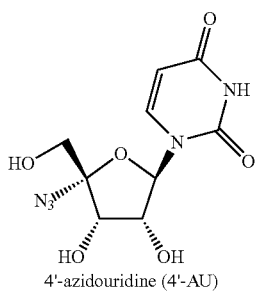

4'-azidouridine (4'-AU)

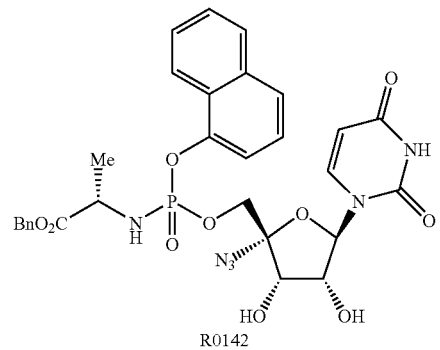

R0142

| | NS5b $IC_{50}$ of NTP (μM) | Replicon $EC_{50}$ (μM) |
|---|---|---|
| R1479 | 0.29 | 1.28 |
| 4'-AU | 0.30 | >100 |
| R0142 | — | 0.22 |

SUMMARY OF THE INVENTION

The present invention is directed toward novel 5'-O-[4-(R,S)-(hetero)aryl-2-oxo-1,3,2-dioxaphosphorinan-2-yl] derivatives of 4'azidouridine, 4'azidocytidine and 1-((2R,3R,4S,5R)-5-azido-3,4-dihydroxy-5-hydroxymethyl-tetrahydro-furan-2-yl)-4-alkylamino-1H-pyrimidin-2-ones and di-acyl derivatives thereof. Compounds of the present invention possesses a structure according to formula I or II.

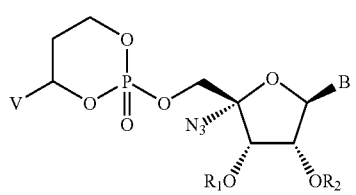

I

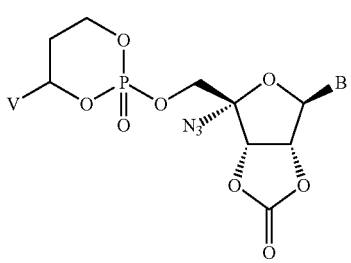

wherein V is phenyl or pyridinyl said phenyl or pyridinyl optionally substituted with one to three substituents selected from the group consisting of halogen, $C_{1-6}$ alkyl, $C_{1-6}$ haloalkyl, $C_{1-6}$ alkoxy, or cyano;

B is

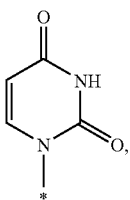

B-1

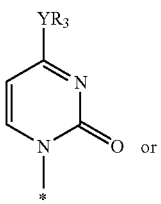

B-2

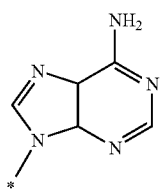

B-3

$R_1$ and $R_2$ are independently selected from H and or $COR_4$;
Y is O or NH;
$R_3$ is $C_1$-$C_6$ alkyl or $COR_4$ and,
$R_4$ is $C_{1-6}$ alkyl, $C_{1-3}$ alkoxy-$C_{1-6}$ alkyl, $C_{3-6}$ cycloalkyl, $C_{3-6}$ cycloalkyl-$C_{1-3}$ alkyl, $C_{1-6}$ alkoxy or heteroaryl wherein the heteroaryl is a five-membered ring containing one or two heteroatoms selected from nitrogen, oxygen or sulfur or pyridine or a six-membered ring with one or two nitrogen atoms; or, a or pharmaceutically acceptable salt thereof.

The present invention further provides a method for treating an HCV infection using compounds of formula I alone or in combination with other antiviral compounds and/or with immunomodulators. The present invention further provides a method for inhibiting the replication of HCV. The present invention further provides compositions containing formula I which are useful in treating HCV infections.

DETAILED DESCRIPTION OF THE INVENTION

Figure 1:
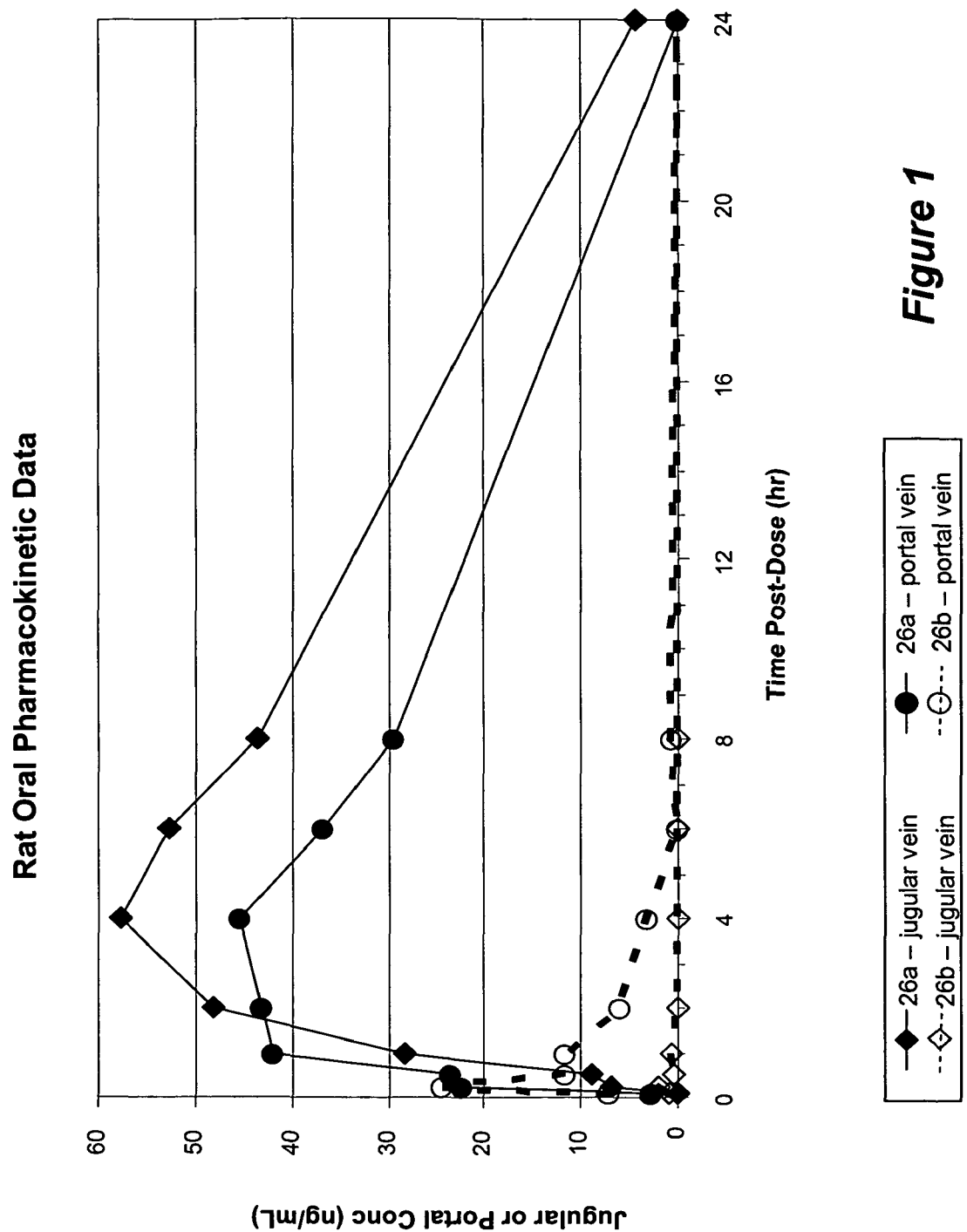
FIG. 1 depicts the data from a pharmacokinetic study comparing absorption of the diester, phosphonate azido-5'-(4-(3-chlorophenyl)-2-oxo-[1,3,2]-dioxaphosphinan-2-yl)-uridine 2',3'-dipropionate (26b), compared to the unesterified phosphonate, 4'-azido-5'-(4-(3-chlorophenyl)-2-oxo-[1,3,2]-dioxaphosphinan-2-yl)-uridine (26a).

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a compound or composition, the term "comprising" means that the compound or composition includes at least the recited features or components, but may also include additional features or components.

It will be understood that the subject to which a compound of the invention is administered need not suffer from a specific traumatic state. Indeed, the compounds of the invention may be administered prophylactically, prior to any development of symptoms. The term "therapeutic", "therapeutically", and permutations of these terms are used to encompass therapeutic, palliative as well as prophylactic uses. Hence, as used herein, by "treating or alleviating the symptoms" is meant reducing, preventing, and/or reversing the symptoms of the individual to which a compound of the invention has been administered, as compared to the symptoms of an individual receiving no such administration.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as *Fieser and Fieser's Reagents for Organic Synthesis*; Wiley & Sons: New York, Volumes 1-21; R. C. LaRock, *Comprehensive Organic Transformations*, $2^{nd}$ edition Wiley-VCH, New York 1999; Comprehensive Organic Synthesis, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

In one embodiment of the present invention there is provided a compound according to general formula I or II as shown in Summary of the Invention wherein $R_1$, $R_2$, B and V are as described herein above. The phrase "as defined herein above" refers to the broadest definition for each group as provided in the Summary of the Invention above. In all other embodiments provided below, substituents which can be present in each embodiment and which are not explicitly defined retain the broadest definition provided in the Summary of the Invention.

In a second embodiment of the present invention there is provided a compound according to general formula I as shown in the Summary of the Invention wherein B is B-1.

In a third embodiment of the present invention there is provided a compound of general formula I as shown in the Summary of the Invention wherein B is B-1 V is optionally substituted phenyl and $R_1$ and $R_2$ are independently hydrogen or $C_{1-6}$ alkyl.

In a fourth embodiment of the present invention there is provided a compound according to general formula I as shown in the Summary of the Invention.

In a fifth embodiment of the present invention there is provided a compound of general formula II according to general formula I as shown in the Summary of the Invention, V is optionally substituted phenyl and B is B-1.

In another embodiment of the present invention there is provided a compound according to general formula I as shown in the Summary of the Invention 1 wherein B is B-1 and V is optionally substituted pyridinyl.

In still another embodiment of the present invention there is provided a compound according to general formula I as shown in the Summary of the Invention wherein B is B-1 and Y is NH and $R_3$ is $C_{1-6}$ alkyl or $R_4CO$. These functionalized purines may serve as prodrugs for the uridine portion, which may be useful for optimizing the lipophilicity as well as masking the hydrogen-bond donor functionality. Thus, 4-acyloxy and 4-alkoxycarbonyloxy derivatives are suitable prodrugs. Furthermore, it is known that certain analogs of cytidine monophosphate are deaminated within cells to the corresponding analogs of uridine monophosphate (Murkarni, E.; Niu, C.; Bao, H.; Steuer, H. M. M.; Whitaker, T.; Nachman, T.; Sofia, M. A.; Wang, P.; Otto, M. J.; Furman, P. A., The Mechanism of Action of β-D-2'-C-Methylcytidine Involves a Second Metabolic Pathway Leading to β-d-2'-C-Methyluridine 5'-Triphosphate, a Potent Inhibitor of the Hepatitis C Virus RNA-Dependent RNA Polymerase., *Antimicrob. Agents Chemotherapy*, 2008, 52, 458-464.). Therefore, 4-O-alkyl and 4-N-alkyl derivatives also are surrogates for the uracil base.

In a sixth embodiment of the present invention there is provided a compound according to general formula I as shown in the Summary of the Invention wherein B is B-2.

In a seventh embodiment of the present invention there is provided a compound according to general formula I as shown in the Summary of the Invention wherein B is B-2 and V is optionally substituted phenyl.

In another embodiment of the present invention there is provided a compound according to general formula I as shown in the Summary of the Invention wherein B is B-2 and V is optionally substituted pyridinyl.

In a eighth embodiment of the present invention there is provided a compound according to general formula I as shown in the Summary of the Invention wherein B is B-3.

In a ninth embodiment of the present invention there is provided a compound according to general formula I as shown in the Summary of the Invention wherein B is B-3 and V is optionally substituted phenyl.

In another embodiment of the present invention there is provided a compound according to general formula I as shown in the Summary of the Invention wherein B is B-3 and V is optionally substituted pyridinyl.

In an tenth embodiment of the present invention there is provide a compound selected from the group consisting of compounds 9 to 61 and 62 in TABLE 1.

In a eleventh embodiment of the present invention there is provided a compound selected from the group consisting of 4'-azido-cis-5'-O-[4-(S)-(3-chlorophenyl)-2-oxo-1,3,2-dioxaphosphorinan-2-yl]uridine 2',3'-O-bis-propionate; 4'-azido-cis-5'-O-[4-(S)-(3-chlorophenyl)-2-oxo-1,3,2-dioxaphosphorinan-2-yl]uridine 2',3'-O-bis-valeroate; and, 4'-azido-cis-5'-O-[4-(S)-(3-chlorophenyl)-2-oxo-1,3,2-dioxaphosphorinan-2-yl]uridine 2',3'-O-bis-isovaleroate.

In a twelfth embodiment of the present invention there is provided a method for treating a disease caused by the Hepatitis C Virus (HCV) virus comprising administering to a patient in need thereof, a therapeutically effective quantity of a compound according to general formula I or II as shown in the Summary of the Invention wherein $R_1$, $R_2$, B and V are as described herein above.

In a thirteenth embodiment of the present invention there is provided a method for treating a disease caused by the Hepatitis C Virus (HCV) virus comprising co-administering to a patient in need thereof, a therapeutically effective quantity of at least one immune system modulator and/or at least one antiviral agent that inhibits replication of HCV. along with compound according to general formula I or H as shown in the Summary of the Invention wherein $R_1$, $R_2$, B and V are as described herein above.

In a fourteenth embodiment of the present invention there is provided a method for treating a disease caused by the Hepatitis C Virus (HCV) virus comprising co-administering to a patient in need thereof, a therapeutically effective quantity of interferon, interleukin, tumor necrosis factor or colony stimulating factor along with compound according to general formula I or H as shown in the Summary of the Invention wherein $R_1$, $R_2$, B and V are as described herein above.

In a fifteenth embodiment of the present invention there is provided a method for treating a disease caused by the Hepatitis C Virus (HCV) virus comprising co-administering to a patient in need thereof, a therapeutically effective quantity of interferon or chemically derivatized interferon along with compound according to general formula I or II as shown in the Summary of the Invention wherein $R_1$, $R_2$, B and V are as described herein above.

In a sixteenth embodiment of the present invention there is provided a method for treating a disease caused by the Hepatitis C Virus (HCV) virus comprising co-administering to a patient in need thereof, a therapeutically effective quantity of an antiviral compound is selected from the group consisting of a HCV protease inhibitor, another HCV polymerase inhibitor, a HCV helicase inhibitor, a HCV primase inhibitor and a HCV fusion inhibitor along with compound according to general formula I or H as shown in the Summary of the Invention wherein $R_1$, $R_2$, B and V are as described herein above.

In a seventeenth embodiment of the present invention there is provided a method of inhibiting replication in HCV comprising administering a therapeutically effective quantity of a compound according to general formula I or H as shown in the Summary of the Invention wherein $R_1$, $R_2$, B and V are as described herein above.

In a eighteenth embodiment of the present invention there is provided a composition containing a therapeutically effective quantity of a compound according to general formula I or H as shown in the Summary of the Invention wherein $R_1$, $R_2$, B and V are as described herein above admixed with at least one pharmaceutically acceptable carrier, diluent or excipient.

The term "alkyl" as used herein without further limitation denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to, lower alkyl groups include methyl, ethyl, propyl, i-propyl, n-butyl, i-butyl, t-butyl, neopentyl, hexyl, and octyl.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents.

"Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term-(ar)alkyl refers to either an unsubstituted alkyl or an aralkyl group. The term (hetero)aryl or (het)aryl refers to either an aryl or a heteroaryl group.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —CH$_2$CH(i-Pr)CH$_2$—), unless otherwise indicated. $C_{0-4}$ alkylene refers to a linear or branched saturated divalent hydrocarbon radical comprising 1-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "cyano" as used herein refers to a carbon linked to a nitrogen by a triple bond, i.e., —C≡N.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 12-fluoroethyl, 2-chloroethyl, 2-bromoethyl, 2,2-dichloroethyl, 3-bromopropyl or 2,2,2-trifluoroethyl.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "alkoxyalkyl" as used herein refers to the radical R'R"—, wherein R' is an alkoxy radical as defined herein, and R" is an alkylene radical as defined herein with the understanding that the attachment point of the alkoxyalkyl moiety will be on the alkylene radical. $C_{1-6}$ alkoxyalkyl denotes a group wherein the alkyl portion is comprised of 1-6 carbon atoms exclusive of carbon atoms in the alkoxy portion of the group. $C_{1-3}$ alkoxy-$C_{1-6}$alkyl denotes a group wherein the alkyl portion is comprised of 1-6 carbon atoms and the alkoxy group is 1-3 carbons. Examples include, but are not limited to, methoxymethyl, methoxyethyl, methoxypropyl, ethoxyethyl, ethoxypropyl, propyloxypropyl, methoxybutyl, ethoxybutyl, butyloxybutyl, t-butyloxybutyl, ethoxypentyl, propyloxypentyl including their isomers.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "cycloalkylalkyl" as used herein refers to the radical R'R"—, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cycloalkyl and R" is $C_{1-3}$ alkylene as defined herein.

The term "alkoxyalkyl" as used herein refers to the radical R'R"—, wherein R' is an alkoxy radical as defined herein, and R" is an alkylene radical as defined herein with the understanding that the attachment point of the alkoxyalkyl moiety will be on the alkylene radical. $C_{1-6}$ alkoxyalkyl denotes a group wherein the alkyl portion is comprised of 1-6 carbon atoms exclusive of carbon atoms in the alkoxy portion of the group. $C_{1-3}$ alkoxy-$C_{1-6}$ alkyl denotes a group wherein the alkyl portion is comprised of 1-6 carbon atoms and the alkoxy group is 1-3 carbons. Examples include, but are not limited to, methoxymethyl, methoxyethyl, methoxypropyl, ethoxyethyl, ethoxypropyl, propyloxypropyl, methoxybutyl, ethoxybutyl, butyloxybutyl, t-butyloxybutyl, ethoxypentyl, propyloxypentyl including their isomers.

The term uracil refers to a compound of formula (i), cytosine refers to a compound of formula (ii) and adenine refers to a compound of formula (iii).

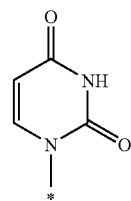

(i)

-continued (ii)

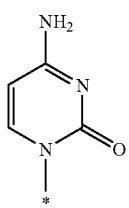

(iii)

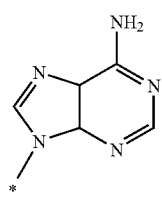

The symbols "*" at the end of a bond or "------" drawn through a bond each refer to the point of attachment of a functional group or other chemical moiety to the rest of the molecule of which it is a part. Thus, for example:

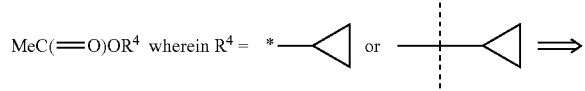

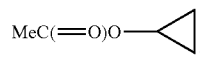

Compounds and Preparation

Despite intense efforts to identify therapies for HCV infections, it remains a disease without a broadly effective therapy. Hepatitis C virus is the leading cause of chronic liver disease throughout the world (Boyer, N. et al. *J. Hepatol.* 2000 32:98-112). Patients infected with HCV are at risk of developing cirrhosis of the liver and subsequent hepatocellular carcinoma and hence HCV is the major indication for liver transplantation.

Examples of representative compounds encompassed by the present invention and within the scope of the invention are provided in the following Table. These examples and the preparations which follow are provided to enable those skilled in the art to more clearly understand and to practice the present invention. They should not be considered as limiting the scope of the invention, but merely as being illustrative and representative thereof.

TABLE 1

| Example | structure | Procedure[1] | $^1$H NMR (500 MHz, DMSO-d$_6$) | MS M + 1 found (calcd) |
|---|---|---|---|---|
| 10 | 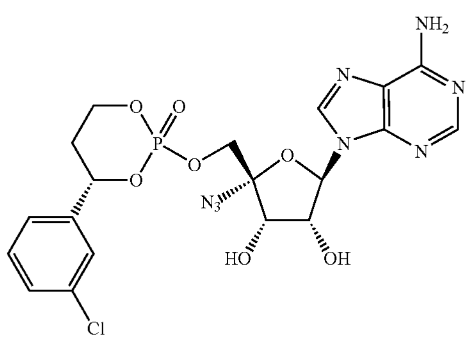 | A | δ 2.1-2.2 (m, 2H), 4.22 (dd, 1H, J = 11, 6 Hz), 4.34 (dd, 1H, J = 11, 6 Hz), 4.35-4.4 (m, 1H), 4.49 (t, 1H, J = 5 Hz), 4.5-4.6 (m, 1H), 5.02 (dd, 1H, J = 11, 6 Hz), 5.71 (dt, 1H, J = 10, 3 Hz), 5.84 (d, 1H, J = 6 Hz), 6.20 (d, 1H, J = 5 Hz), 6.21 (d, 1H, J = 6 Hz), 7.3-7.4 (m, 3H), 7.4-7.45 (m, 2H), 7.50 (s, 1H), 8.11 (s, 1H), 8.42 (s, 1H) | 539.4 (539.1) |
| 11 | 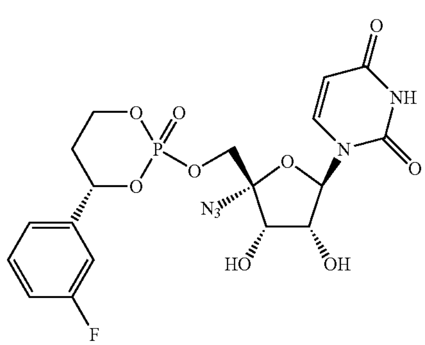 | A | δ 2.16-2.20 (m, 1H), 2.23-2.28 (m, 1H), 4.12-4.23 (m, 3H), 4.33-4.37 (m, 1H), 4.44-4.45 (m, 1H), 4.53-4.56 (m, 1H), 5.59-5.65 (m, 1H), 5.73-5.74 (m, 2H), 6.04-6.07 (m, 2H), 7.18-7.21 (m, 1H), 7.27-7.31 (m, 2H), 7.42-7.48 (m, 1H), 7.68 (dd, 1H, J = 10, 1 Hz), 11.47 (s, 1H) | 500.9 (500.1) |

TABLE 1-continued

| Example | structure | Procedure[1] | $^1$H NMR (500 MHz, DMSO-d$_6$) | MS M + 1 found (calcd) |
|---|---|---|---|---|
| 12 | 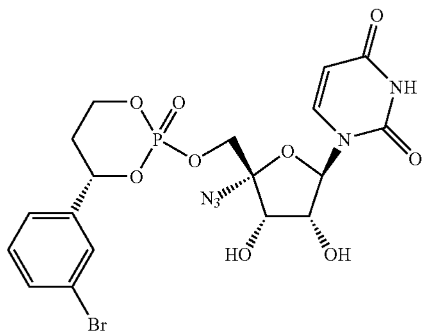 | A | δ 2.16-2.20 (m, 1H), 2.25-2.29 (m, 1H), 4.11-4.23 (m, 3H), 4.34-4.37 (m, 1H), 4.42-4.46 (m, 1H), 4.51-4.56 (m, 1H), 5.60-5.65 (m, 1H), 5.70-5.75 (m, 2H), 6.04-6.09 (m, 2H), 7.35-7.39 (m, 1H), 7.43-7.46 (m, 1H), 7.55-7.58 (m, 1H), 7.64-7.66 (m, 1H), 7.69 (d, 1H, J = 3 Hz), 11.47 (s, 1H) | 560.4 (560.0) |
| 13 | 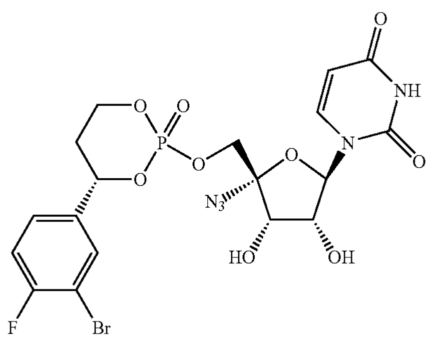 | A | δ 2.16-2.19 (m, 1H), 2.27-2.30 (m, 1H), 4.11-4.23 (m, 3H), 4.35-4.38 (m, 1H), 4.42-4.46 (m, 1H), 4.50-4.54 (m, 1H), 5.60-5.66 (m, 1H), 5.71-5.75 (m, 2H), 6.04-6.07 (m, 2H), 7.39-7.43 (m, 1H), 7.48-7.52 (m, 1H), 7.69 (dd, 1H, J = 11, 3 Hz), 7.78-7.81 (m, 1H), 11.47 (s, 1H) | 580.6 (580.0) |
| 14 | 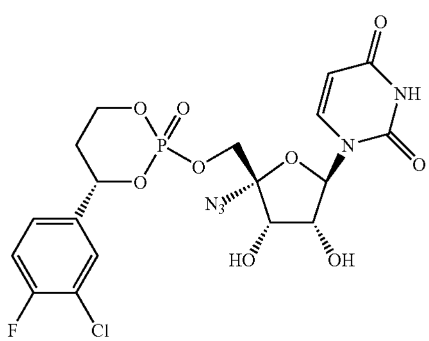 | A | δ 2.16-2.19 (m, 1H), 2.27-2.30 (m, 1H), 4.12-4.23 (m, 3H), 4.35-4.38 (m, 1H), 4.42-4.46 (m, 1H), 4.50-4.55 (m, 1H), 5.60-5.65 (m, 1H), 5.72-5.75 (m, 2H), 6.04-6.08 (m, 2H), 7.44-7.47 (m, 2H), 7.67-7.70 (m, 2H), 11.47 (s, 1H) | 534.4 (533.1) |
| 15 | 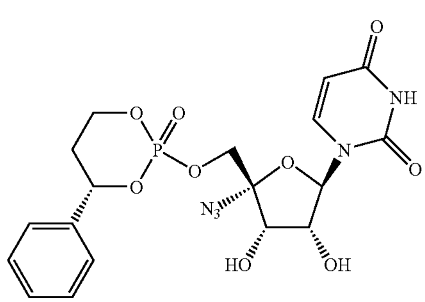 | A | δ 2.12-2.16 (m, 1H), 2.27-2.30 (m, 1H), 4.12-4.20 (m, 3H), 4.21-4.24 (m, 1H), 4.33-4.36 (m, 1H), 4.36-4.40 (m, 1H), 4.55-4.57 (m, 1H), 5.57 (d, 1H, J = 8 Hz), 5.69-5.72 (m, 1H), 5.74 (d, 1H, J = 6 Hz), 6.04-6.08 (m, 2H), 7.35-7.45 (m, 5H), 7.67-7.68 (d, 1H, J = 8 Hz), 11.46 (s, 1H) | 482.4 (482.1) |

TABLE 1-continued

| Example | structure | Procedure[1] | $^1$H NMR (500 MHz, DMSO-d$_6$) | MS M + 1 found (calcd) |
|---|---|---|---|---|
| 16 | 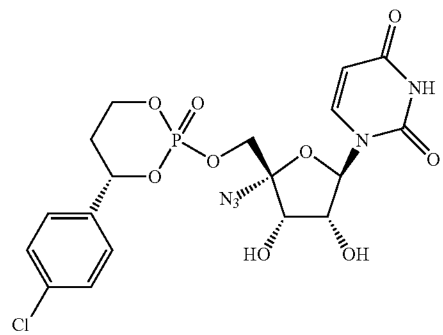 | A | δ 2.13-2.17 (m, 1H), 2.23-2.28 (m, 1H), 4.11-4.24 (m, 3H), 4.34-4.37 (m, 1H), 4.42-4.47 (m, 1H), 4.52-4.55 (m, 1H), 5.60-5.66 (m, 1H), 5.71-5.75 (m, 2H), 6.03-6.05 (m, 2H), 7.46-7.47 (m, 4H), 7.69 (dd, 1H, J = 11, 3 Hz), 11.48 (s, 1H) | 516.6 (516.1) |
| 17 | 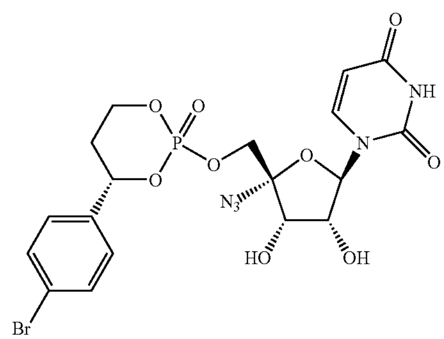 | A | δ 2.13-2.16 (m, 1H), 2.23-2.26 (m, 1H), 4.12-4.24 (m, 3H), 4.34-4.37 (m, 1H), 4.43-4.47 (m, 1H), 4.53-4.55 (m, 1H), 5.60-5.66 (m, 1H), 5.71 (d, 1H, J = 11 Hz), 5.74 (d, 1H, J = 6.5 Hz), 6.03-6.06 (m, 2H), 7.39-7.41 (m, 2H), 7.59-7.62 (m, 2H), 7.68-7.70 (dd, 1H, J = 11, 3 Hz), 11.48 (s, 1H) | 562.4 (562.0) |
| 18 | 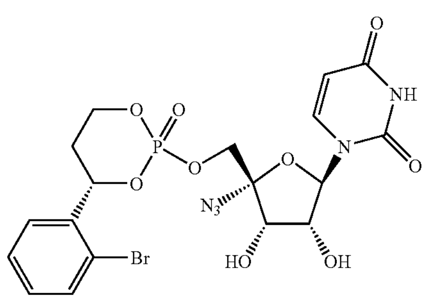 | A | δ 2.22-2.28 (m, 2H), 4.16-4.27 (m, 3H), 4.35-4.39 (m, 1H), 4.46-4.49 (m, 1H), 4.61-4.64 (m, 1H), 5.60-5.66 (m, 1H), 5.75 (d, 1H, J = 6 Hz), 5.82-5.85 (m, 1H), 6.05-6.08 (m, 2H), 7.31-7.36 (m, 1H), 7.45-7.49 (m, 1H), 7.60-7.63 (m, 1H), 7.66-7.71 (m, 2H), 11.47 (s, 1H) | 562.4 (562.0) |
| 19 | 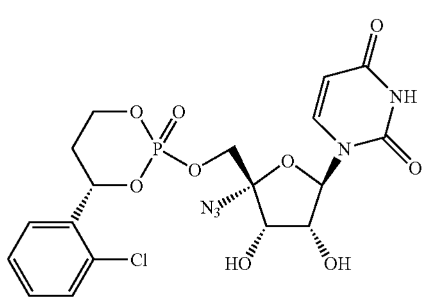 | A | δ 2.18-2.21 (m, 1H), 2.27-2.30 (m, 1H), 4.15-4.26 (m, 3H), 4.35-4.38 (m, 1H), 4.45-4.50 (m, 1H), 4.62-4.65 (m, 1H), 5.59-5.65 (m, 1H), 5.75 (d, 1H, J = 6 Hz), 5.90-5.93 (m, 1H), 6.04-6.08 (m, 2H), 7.41-7.44 (m, 1H), 7.45-7.52 (m, 1H), 7.61-7.64 (m, 1H), 7.69 (d, 1H, J = 8 Hz), 11.47 (s, 1H) | 516.6 (516.1) |

TABLE 1-continued

| Example | structure | Procedure[1] | $^1$H NMR (500 MHz, DMSO-d$_6$) | MS M + 1 found (calcd) |
|---|---|---|---|---|
| 20 | 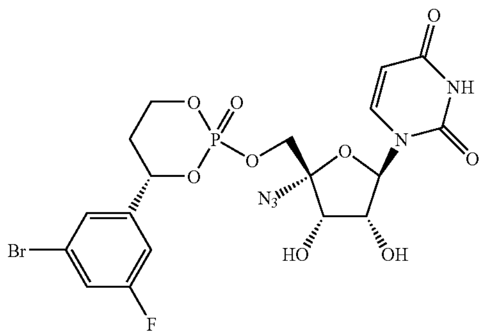 | A | δ 2.13-2.16 (m, 1H), 2.34-2.50 (m, 1H), 4.10-4.23 (m, 3H), 4.33-4.37 (m, 1H), 4.43-4.48 (m, 1H), 4.58-4.63 (m, 1H), 5.57-5.66 (m, 1H), 5.74 (d, 1H, J = 6 Hz), 5.86-5.89 (m, 1H), 6.03-6.07 (m, 2H), 7.26-7.45 (m, 2H), 7.63 (dd, 1H, J = 11, 3 Hz), 7.67-7.68 (m, 1H), 11.47 (s, 1H) | 580.9 (580.0) |
| 21 | 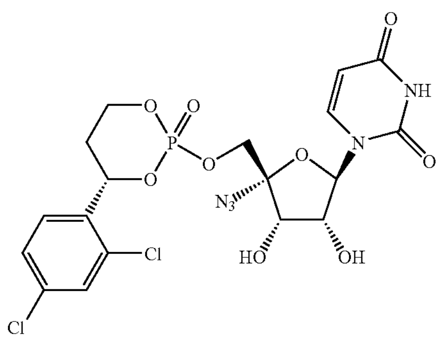 | A | δ 2.08-2.18 (m, 1H), 2.21-2.28 (m, 1H), 4.15-4.26 (m, 3H), 4.35-4.39 (m, 1H), 4.45-4.49 (m, 1H), 4.62-4.64 (m, 1H), 5.62-5.67 (m, 1H), 5.74 (d, 1H, J = 7 Hz), 5.88-5.90 (m, 1H), 6.03-6.06 (m, 2H), 7.50-7.53 (m, 1H), 7.53-7.64 (m, 1H), 7.69-7.71 (m, 2H), 11.48 (s, 1H) | 550.4 (550.0) |
| 22 | 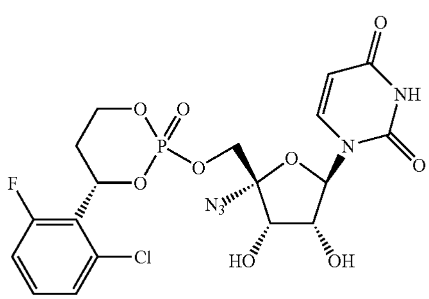 | A | δ 2.09-2.10 (m, 1H), 2.61-2.79 (m, 1H), 4.07-4.11 (m, 1H), 4.16-4.22 (m, 2H), 4.31-4.32 (m, 1H), 4.45-4.56 (m, 1H), 4.62-4.69 (m, 1H), 5.55-5.66 (m, 1H), 5.73-5.74 (m, 1H), 6.03-6.09 (m, 3H), 7.30-7.35 (m, 1H), 7.40-7.42 (m, 1H), 7.48-7.52 (m, 1H), 7.65 (d, 1H, J = 8 Hz), 11.47 (s, 1H) | 534.4 (534.1) |
| 23 | 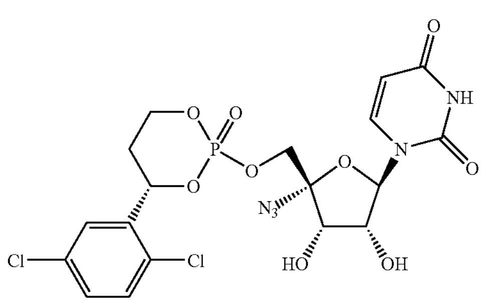 | A | δ 2.20-2.23 (m, 1H), 2.28-2.36 (m, 1H), 4.16-4.35 (m, 3H), 4.36-4.39 (m, 1H), 4.44-4.48 (m, 1H), 4.62-4.64 (m, 1H), 5.61-5.65 (m, 1H), 5.74 (d, 1H, J = 7 Hz), 5.89 (dd, 1H, J = 11, 3 Hz), 6.06-6.10 (m, 2H), 7.48-7.51 (m, 1H), 7.55 (dd, 1H, J = 12, 3 Hz), 7.65-7.72 (m, 2H), 11.46 (s, 1H) | 550.4 (550.0) |

TABLE 1-continued

| Example | structure | Procedure[1] | $^1$H NMR (500 MHz, DMSO-d$_6$) | MS M + 1 found (calcd) |
|---|---|---|---|---|
| 24 | 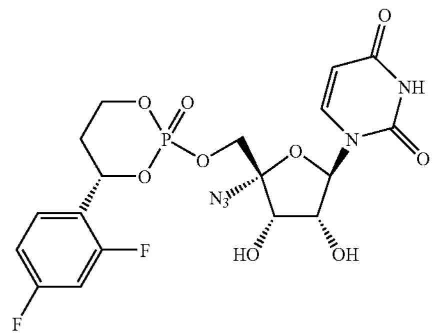 | A | δ 2.09-2.14 (m, 1H), 2.40-2.44 (m, 1H), 4.10-4.23 (m, 3H), 4.33-4.36 (m, 1H), 4.43-4.49 (m, 1H), 4.58-4.61 (m, 1H), 5.60-5.66 (m, 1H), 5.74 (d, 1H, J = 6 Hz), 5.88 (dd, 1H, J = 11, 3 Hz), 6.03-6.05 (m, 2H), 7.14-7.17 (m, 1H), 7.30-7.35 (m, 1H), 7.61-7.65 (m, 1H), 7.68 (dd, 1H, J = 10, 2 Hz), 11.47 (s, 1H) | 518.6 (518.1) |
| 25 | 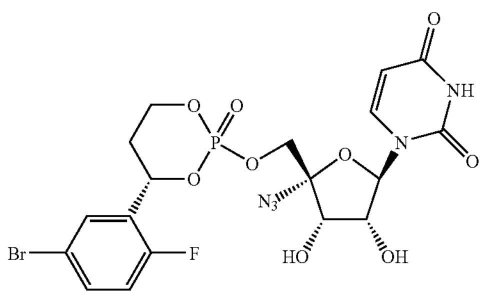 | A | δ 2.14-2.17 (m, 1H), 2.36-2.43 (m, 1H), 4.11-4.24 (m, 3H), 4.33-4.39 (m, 1H), 4.44-4.47 (m, 1H), 4.58-4.62 (m, 1H), 5.60-5.65 (m, 1H), 5.73 (d, 1H, J = 6 Hz), 5.89 (dd, 1H, J = 11, 3 Hz), 6.05-6.08 (m, 2H), 7.25-7.29 (m, 1H), 7.62-7.65 (m, 1H), 7.65-7.70 (m, 1H), 7.72-7.76 (m, 1H), 11.46 (s, 1H) | 580.6 (580.0) |
| 26 | 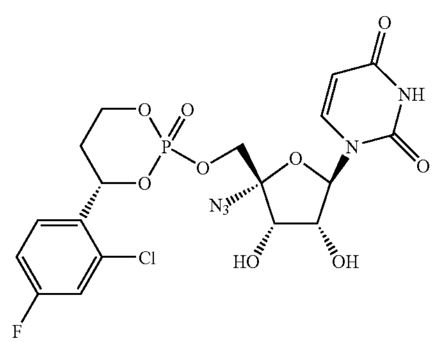 | A | δ 2.16-2.19 (m, 1H), 2.29-2.33 (m, 1H), 4.14-4.25 (m, 3H), 4.35-4.38 (m, 1H), 4.43-4.49 (m, 1H), 4.60-4.64 (m, 1H), 5.61-5.66 (m, 1H), 5.75 (d, 1H, J = 7 Hz), 5.87-5.90 (m, 1H), 6.03-6.06 (m, 2H), 7.23-7.34 (m, 1H), 7.51-7.54 (m, 1H), 7.65-7.71 (m, 2H), 11.47 (s, 1H) | 534.4 (534.1) |
| 27 | 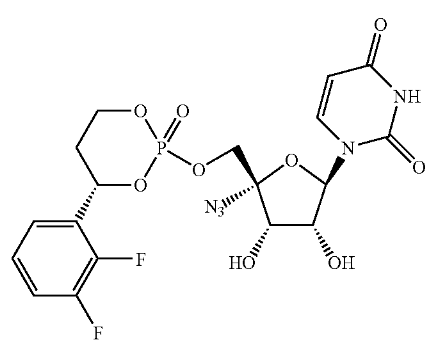 | A | δ 2.17-2.20 (m, 1H), 2.39-2.41 (m, 1H), 4.11-4.23 (m, 3H), 4.33-4.36 (m, 1H), 4.46-4.47 (m, 1H), 4.62-4.63 (m, 1H), 5.60-5.65 (m, 1H), 5.74 (d, 1H, J = 7 Hz), 5.95 (dd, 1H, J = 12, 3 Hz), 6.03-6.06 (m, 2H), 7.27-7.29 (m, 1H), 7.37-7.39 (m, 1H), 7.46-7.49 (m, 1H), 7.67-7.69 (m, 1H), 11.47 (s, 1H) | 518.6 (518.1) |

TABLE 1-continued

| Example | structure | Procedure[1] | $^1$H NMR (500 MHz, DMSO-$d_6$) | MS M + 1 found (calcd) |
|---|---|---|---|---|
| 28 | 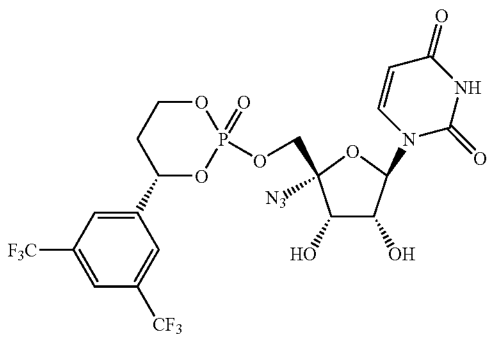 | A | δ 2.08-2.36 (m, 2H), 4.17-4.24 (m, 3H), 4.33-4.38 (m, 1H), 4.45-4.49 (m, 1H), 4.54-4.57 (m, 1H), 5.61 (d, 1H, J = 8 Hz), 5.73 (dd, 1H, J = 6, 3 Hz), 5.94-5.97 (m, 1H), 6.04-6.07 (m, 2H), 7.67-7.71 (m, 1H), 8.12-8.13 (m, 2H), 11.45 (s, 1H) | 618.4 (618.1) |
| 29 | 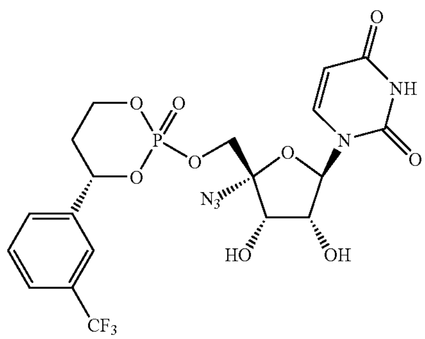 | A | δ 2.22-2.32 (m, 2H), 4.12-4.15 (m, 3H), 4.33-4.38 (m, 1H), 4.45-4.47 (m, 1H), 4.55-4.58 (m, 1H), 5.59-5.63 (m, 1H), 5.73 (dd, 1H, J = 8, 1 Hz), 5.83 (dd, 1H, J = 11, 3 Hz), 6.04-6.06 (m, 2H), 7.64-7.70 (m, 2H), 7.72-7.79 (m, 3H), 11.46 (s, 1H) | 550.4 (550.1) |
| 30 | 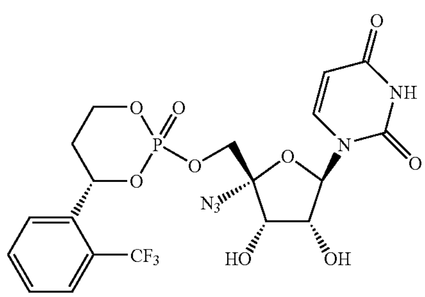 | A | δ 2.06-2.09 (m, 1H), 2.39-2.42 (m, 1H), 4.18-4.28 (m, 3H), 4.36-4.40 (m, 1H), 4.44-4.49 (m, 1H), 4.63-4.65 (m, 1H), 5.59-5.65 (m, 1H), 5.75 (dd, 1H, J = 6, 2 Hz), 5.85 (d, 1H, J = 11 Hz), 6.05-6.09 (m, 2H), 7.60-7.64 (m, 1H), 7.70 (dd, 1H, J = 10, 2 Hz), 7.76-7.79 (m, 1H), 7.80-7.89 (m, 1H), 11.47 (s, 1H) | 550.4 (550.1) |
| 31 | 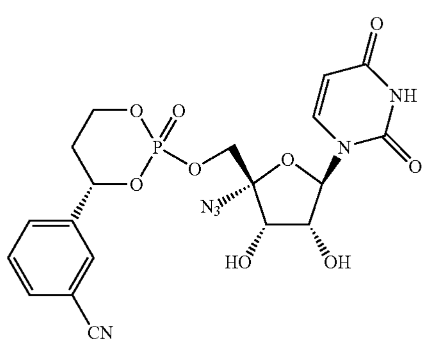 | A | δ 2.20-2.31 (m, 2H), 4.12-4.26 (m, 3H), 4.34-4.38 (m, 1H), 4.44-4.48 (m, 1H), 4.53-4.57 (m, 1H), 5.60-5.65 (m, 1H), 5.75 (d, 1H, J = 7 Hz), 5.79 (d, 1H, J = 10 Hz), 6.04-6.07 (m, 2H), 7.61-7.68 (m, 1H), 7.69 (d, 1H, J = 1.5 Hz), 7.77-7.79 (m, 1H), 7.83-7.85 (m, 1H), 7.92 (d, 1H, J = 6 Hz), 11.46 (s, 1H) | 507.1 (507.1) |

TABLE 1-continued

| Example | structure | Procedure[1] | $^1$H NMR (500 MHz, DMSO-$d_6$) | MS M + 1 found (calcd) |
|---|---|---|---|---|
| 32 | 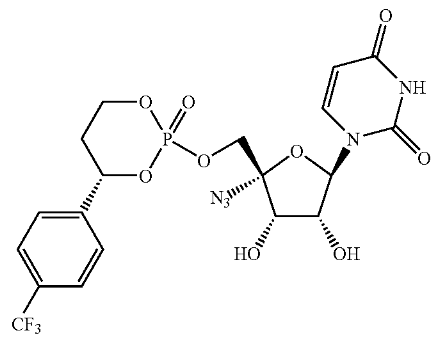 | A | δ 2.23-2.28 (m, 2H), 4.14-4.25 (m, 3H), 4.35-4.38 (m, 1H), 4.46-4.47 (m, 1H), 4.55-4.59 (m, 1H), 5.60-5.65 (m, 1H), 5.74-5.76 (m, 1H), 5.84 (dd, 1H, J = 11, 4 Hz), 6.03-6.07 (m, 2H), 7.65-7.70 (m, 3H), 7.76-7.79 (m, 2H), 11.47 (s, 1) | 550.4 (550.1) |
| 33 | 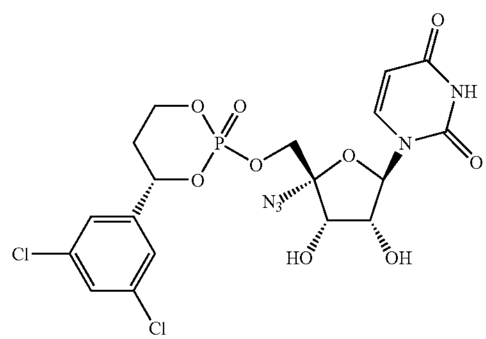 | A | δ 2.20-2.38 (m, 2H), 4.05-4.60 (m, 4H), 5.59-5.74 (m, 4H), 6.05 (m, 2H), 7.48 (m, 2H), 7.65 (m, 1H), 7.58 (m, 1H), 11.40 (s, 1H) | 550.4 (550.0) |
| 34 | 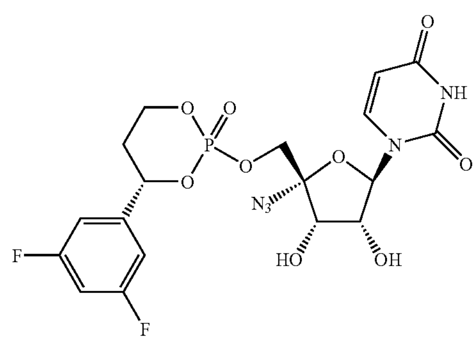 | A | δ 2.20-2.38 (m, 2H), 4.08-4.60 (m, 4H), 5.60 (d, 1H, J = 8.2 Hz), 5.73 (m, 2H), 6.03 (m, 2H), 6.05 (m, 2H), 7.17 (m, 3H), 7.7 (d, 1H, J = 8.2 Hz), 7.65 (m, 1H), 11.40 (s, 1H) | 518.6 (518.1) |
| 35 | 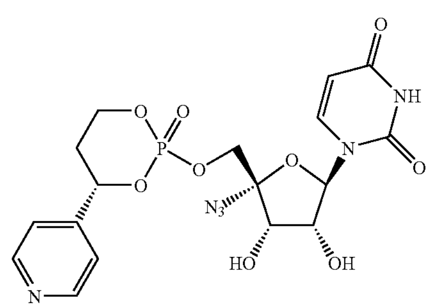 | A | δ 2.15-2.35 (m, 2H), 4.08-4.60 (m, 4H), 5.60 (d, 1H, J = 7.9 Hz), 5.73 (m, 2H), 6.03 (m, 2H), 7.4 (m, 2H), 7.68 (d, 1H, J = 8.2 Hz), 8.6 (m, 2H), 11.30 (s, 1H) | 483.4 (483.1) |

TABLE 1-continued

| Example | structure | Procedure[1] | $^1$H NMR (500 MHz, DMSO-d$_6$) | MS M + 1 found (calcd) |
|---|---|---|---|---|
| 36 | 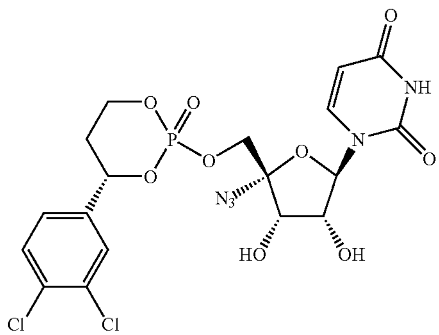 | A | δ 2.18-2.38 (m, 2H), 4.08-4.60 (m, 4H), 5.60 (d, 1H, J = 7.9 Hz), 5.73 (m, 2H), 6.03 (m, 2H), 7.4 (m, 1H), 7.65-7.71 (m, 3H), 11.40 (s, 1H) | 550.4 (550.0) |
| 37 | 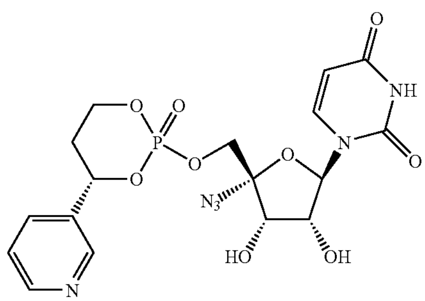 | A | δ 2.12-2.42 (m, 2H), 4.08-4.60 (m, 4H), 5.60 (m, 1H), 5.74-5.80 (m, 2H), 6.04 (m, 2H), 7.4 (m, 1H), 7.65 (m, 1H), 7.85 (m, 1H), 8.55 (m, 1H), 8.65 (m, 1H), 11.40 (s, 1H) | 483.4 (483.1) |
| 38 | 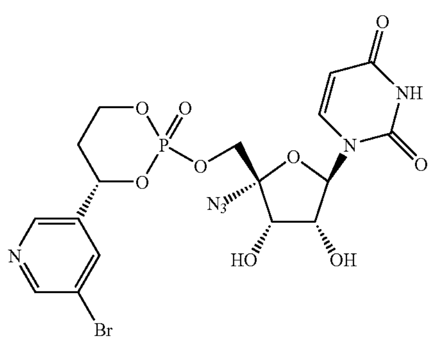 | A | δ 2.20-2.42 (m, 2H), 4.08-4.60 (m, 4H), 5.60 (m, 1H), 5.74 (m, 1H), 5.80 (m, 1H), 6.04 (m, 2H), 7.6 (m, 1H), 8.12 (m, 1H), 8.65 (m, 1H), 8.70 (m, 1H), 11.40 (s, 1H) | 561.4 (561.0) |
| 39 | 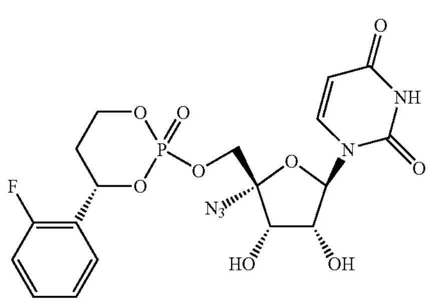 | A | δ 2.04-2..42 (m, 2H), 4.08-4.66 (m, 4H), 5.60 (m, 1H), 5.74 (m, 2H), 5.85 (m, 1H), 6.04 (m, 2H), 7.30 (m, 2H), 7.40-7.65 (m, 2H), 7.80 (m, 1H), 8.55 (m, 1H), 8.65 (m, 1H), 11.50 (s, 1H) | 500.9 (500.1) |

TABLE 1-continued

| Example | structure | Procedure[1] | $^1$H NMR (500 MHz, DMSO-d6) | MS M + 1 found (calcd) |
|---|---|---|---|---|
| 40 | 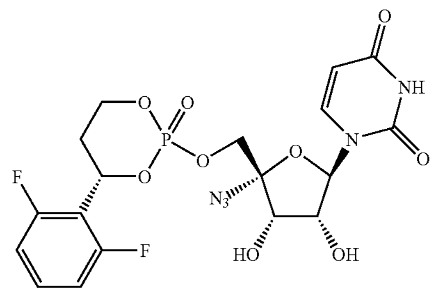 | A | δ 2.04-2.18 (m, 1H), 2.58-2.75 (m, 1H), 4.08-4.75 (m, 6H), 5.50-5.70 (m, 2H), 5.85 (m, 1H), 6.04 (m, 2H), 7.20 (m, 2H), 7.50 (m, 1H), 7.65 (m, 1H), 8.55 (m, 1H), 8.65 (m, 1H), 11.40 (s, 1H) | 518.6 (518.1) |
| 41 | 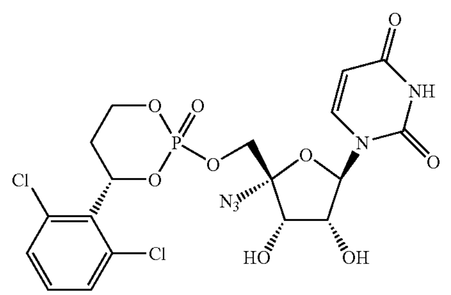 | A | δ 2.00 (m, 1H), 2.90 (m, 1H), 4.08-4.75 (m, 6H), 5.50 (m, 1H), 5.75 (m, 1H), 6.00-6.10 (m, 2H), 6.25-6.30 (m, 1H), 7.40 (m, 2H), 7.60 (m, 2H), 7.65 (m, 1H), 11.50 (s, 1H) | 550.4 (550.0) |
| 42 | 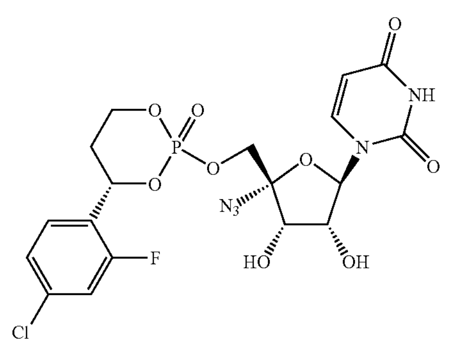 | A | δ 2.18 (m, 1H), 2.40 (m, 1H), 4.08-4.65 (m, 6H), 5.60 (m, 1H), 5.75 (m, 1H), 5.85 (m, 1H), 6.00-6.10 (m, 2H), 7.35 (m, 2H), 7.50 (m, 1H), 7.60 (m, 1H), 7.65 (m, 1H), 11.45 (s, 1H) | 534.4 (534.1) |
| 43 | 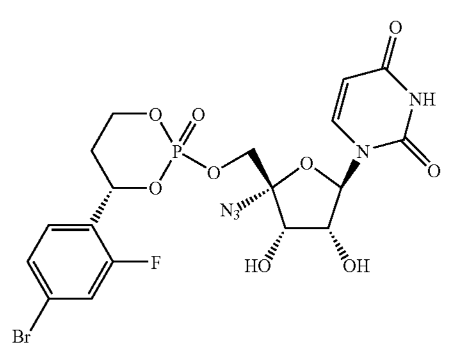 | A | δ 2.18 (m, 1H), 2.40 (m, 1H), 4.08-4.65 (m, 6H), 5.65 (m, 1H), 5.78 (m, 1H), 5.90 (m, 1H), 6.00-6.10 (m, 2H), 7.50 (m, 2H), 7.50 (m, 1H), 7.7 (m, 3H), 11.45 (s, 1H) | 580.9 (580.0) |

TABLE 1-continued

| Example | structure | Procedure[1] | $^1$H NMR (500 MHz, DMSO-d$_6$) | MS M + 1 found (calcd) |
|---|---|---|---|---|
| 44 | 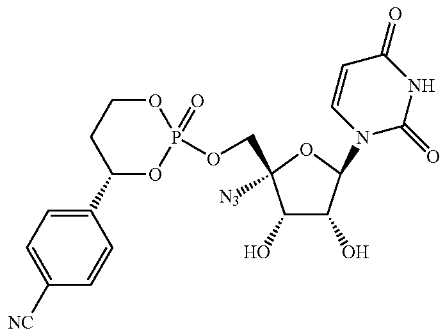 | A | δ 2.05 (m, 2H), 4.08-4.65 (m, 6H), 5.65 (m, 1H), 5.78 (m, 1H), 5.92 (m, 1H), 6.00-6.10 (m, 2H), 7.60 (m, 2H), 7.50-7.55 (m, 3H), 7.90 (m, 2H), 11.45 (s, 1H) | 507.4 (507.1) |
| 45 | 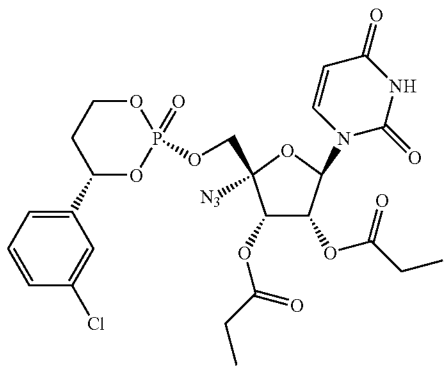 | B | δ 1.02-1.06 (m, 6H), 2.19-2.42 (m, 6H), 4.38 (d, 2H, J = 6 Hz), 4.4-4.5 (m, 1H), 4.53-4.57 (m, 1H), 5.62 (dd, 1H, J = 7, 4 Hz), 5.68 (dd, 1H, J = 8, 2 Hz), 5.73-5.76 (m, 2H), 6.08 (d, 1H, J = 4 Hz), 7.38-7.46 (m, 3H), 7.50 (s, 1H), 7.81 (d, 1H, J = 8 Hz), 11.57 (d, 1H, J = 2 Hz) | 628.9 (628.1) |
| 46 | 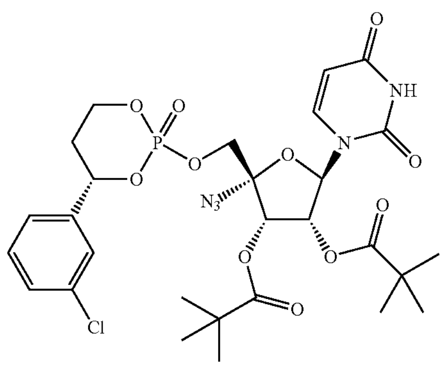 | B | δ 1.17 (s, 9H), 1.19 (s, 9H), 2.21-2.28 (m, 2H), 4.31-4.34 (m, 1H), 4.37-4.46 (m, 2H), 4.55-4.56 (m, 1H), 5.56 (dd, 1H, J = 10, 3 Hz), 5.66 (d, 1H, J = 8 Hz), 5.74 (m, 2H), 5.98 (d, 1H, J = 3 Hz), 7.38-7.43 (m, 3H), 7.50 (s, 1H), 7.79 (d, 1H, J = 9 Hz), 11.56 (s, 1H) | 684.6 (684.2) |
| 47 | 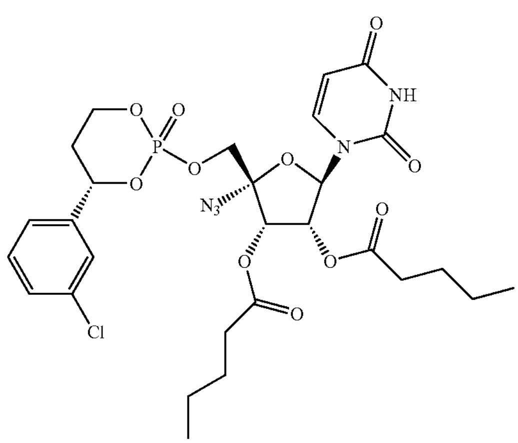 | B | δ 0.83-0.87 (m, 6H), 1.25-1.32 (m, 4H), 1.47-1.54 (m, 4H), 2.21-2.25 (m, 2H), 2.31-2.38 (m, 4H), 4.36 (d, 2H, J = 7 Hz), 4.38-4.43 (m, 1H), 4.54-4.56 (m, 1H), 5.60-5.62 (m, 1H), 5.65 (d, 1H, J = 8 Hz), 5.72-5.75 (m, 2H), 6.05 (d, 1H, J = 4 Hz), 7.38-7.44 (m, 3H), 7.50 (s, 1H), 7.77 (d, 1H, J = 8 Hz), 11.57 (s, 1H) | 684.6 (684.2) |

TABLE 1-continued

| Example | structure | Procedure[1] | $^1$H NMR (500 MHz, DMSO-d$_6$) | MS M + 1 found (calcd) |
|---|---|---|---|---|
| 48 | 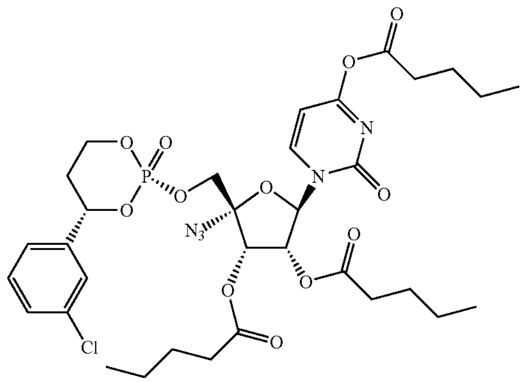 | B | δ 0.80-0.87 (m, 9H), 1.22-1.35 (m, 6H), 1.44-1.55 (m, 6H), 2.1-2.4 (m, 6H), 2.7-2.8 (m, 2H), 4.36 (d, 2H, J = 7 Hz), 4.3-4.6 (m, 2H), 5.63-5.75 (m, 3H), 5.87 (d, 1H, J = 8 Hz), 6.10 (d, 1H, J = 3 Hz), 7.36-7.47 (m, 3H), 7.49 (s, 1H), 7.91 (d, 1H, J = 8 Hz) | 768.6 (768.2) |
| 49 | 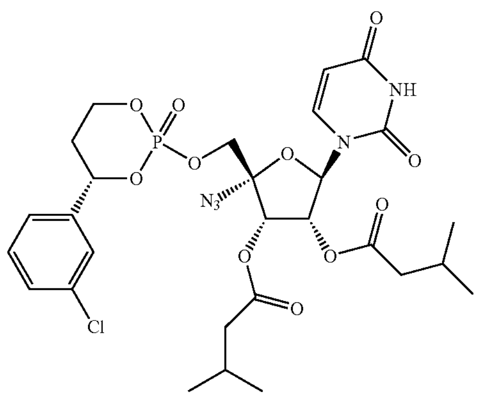 | B | δ 0.87-0.91 (m, 12H), 1.82-2.10 (m, 2H), 2.20-2.50 (m, 6H), 4.30-4.60 (m, 4H), 5.60-5.80 (m, 4H), 6.04 (d, 1H, J = 3.5 Hz), 7.39-7.48 (m, 3H), 7.79 (d, 1H, J = 7.9 Hz), 11.55 (s, 1H) | 684.6 (684.2) |
| 50 | 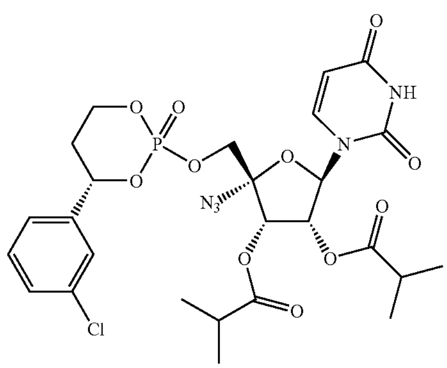 | B | δ 1.08-1.11 (m, 12H), 2.18-2.38 (m, 2H), 2.50-2.61 (m, 2H), 4.30-4.60 (m, 4H), 5.60-5.80 (m, 4H), 6.04 (d, 1H, J = 3.2 Hz), 7.39-7.48 (m, 3H), 7.79 (d, 1H, J = 7.9 Hz), 11.55 (s, 1H) | 656.6 (656.1) |
| 51 | 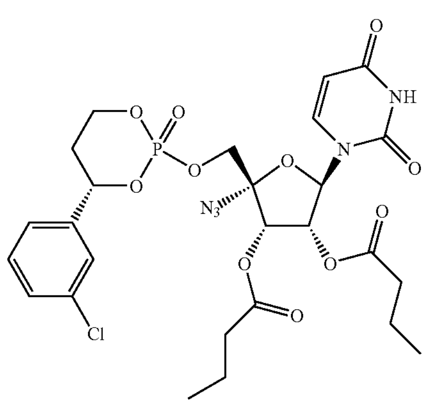 | B | δ 0.84-0.90 (m, 6H), 1.49-1.57 (m, 4H), 2.28-2.50 (m, 6H), 4.35-4.60 (m, 4H), 5.60-5.72 (m, 4H), 6.05 (d, 1H, J = 3.5 Hz), 7.41-7.48 (m, 3H), 7.78 (d, 1H, J = 8.1 Hz), 11.54 (s, 1H) | 656.6 (656.1) |

TABLE 1-continued

| Example | structure | Procedure[1] | $^1$H NMR (500 MHz, DMSO-d$_6$) | MS M + 1 found (calcd) |
|---|---|---|---|---|
| 52 | 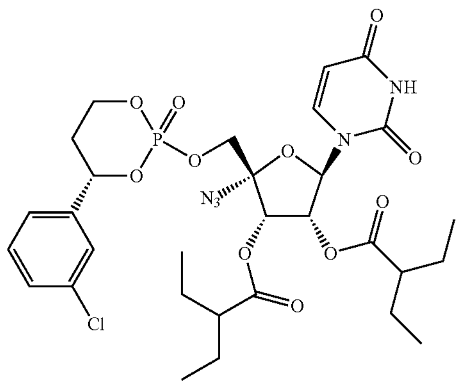 | C | δ 0.80-0.95 (m, 12H), 1.40-1.60 (m, 8H), 2.15-2.35 (m, 4H), 4.30-4.60 (m, 4H), 5.60-5.80 (m, 4H), 6.02 (m, 1H), 7.385-7.453 (m, 3H), 7.5 (s, 1H), 7.80 (m, 1H), 11.55 (s, 1H) | 712.1 (712.2) |
| 53 | 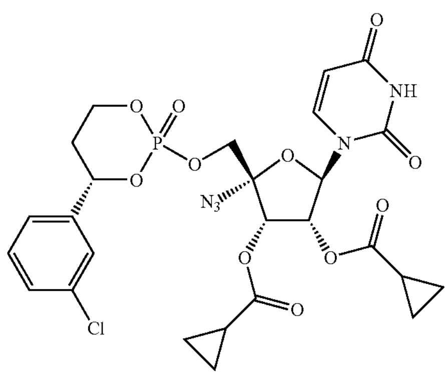 | C | δ 0.89-1.06 (m, 8H), 1.652-1.672 (m, 2H), 2.20-2.50 (m, 2H), 4.32-4.60 (m, 4H), 5.56-5.74 (m, 4H), 6.06 (d, 1H, J = 3.2 Hz), 7.41-7.48 (m, 3H), 7.79 (d, 1H, J = 7.9 Hz), 11.52 (s, 1H) | 652.6 (652.6) |
| 54 | 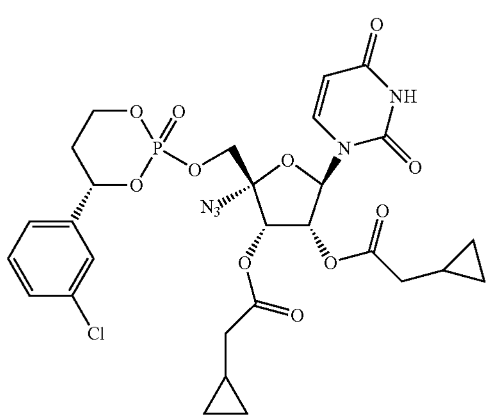 | C | δ 0.14-0.16 (m, 4H), 0.47-0.48 (m, 4H), 0.93-0.96 (m, 2H), 2.19-2.33 (m, 6H), 4.38 (d, 2H, J = 6 Hz), 4.39-4.44 (m, 1H), 4.55-4.57 (m, 1H), 5.63-5.67 (m, 2H), 5.74-5.76 (m, 2H), 6.08 (d, 1H, J = 4 Hz), 7.38-7.44 (m, 3H), 7.50 (s, 1H), 7.80 (d, 1H, J = 8 Hz), 11.57 (s, 1H) | 680.6 (680.1) |

TABLE 1-continued

| Example | structure | Procedure[1] | $^1$H NMR (500 MHz, DMSO-d$_6$) | MS M + 1 found (calcd) |
|---|---|---|---|---|
| 55 | 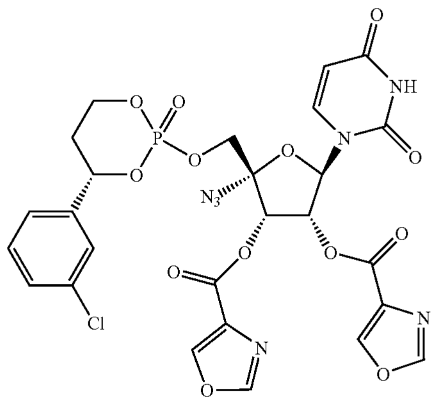 | C | δ 2.20-2.40 (m, 2H), 4.32-4.60 (m, 4H), 5.64-5.8 (m, 2H), 5.95-6.05 (m, 2H), 6.25 (m, 1H), 7.35-7.55 (m, 3H), 7.88 (m, 1H), 8.6 (s, 2H), 8.80 (m, 2H), 11.52 (s, 1H) | 706.6 (706.1) |
| 56 | 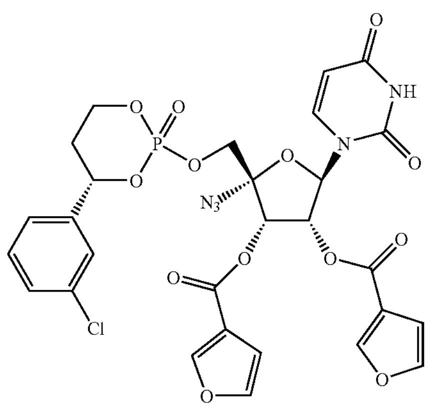 | C | δ 2.10-2.40 (m, 2H), 4.32-4.65 (m, 4H), 5.64-5.8 (m, 2H), 5.95-6.05 (m, 2H), 6.25 (m, 1H), 7.35-7.55 (m, 3H), 7.88-7.9 (m, 3H), 8.3-8.4 (m, 2H), 11.60 (s, 1H) | 704.6 (704.1) |
| 57 | 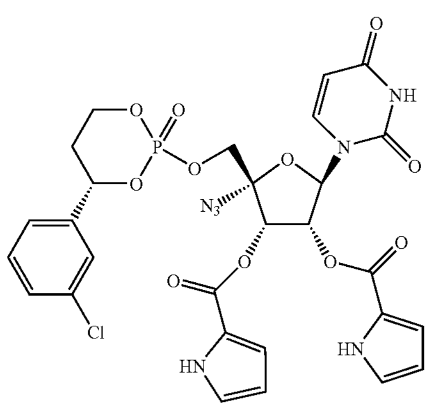 | C | δ 2.16-2.29 (m, 2H), 4.41-4.44 (m, 2H), 4.53-4.55 (m, 1H), 5.68 (d, 1H, J = 8 Hz), 5.71-5.75 (m, 1H), 5.82-5.84 (m, 1H), 5.93 (d, 1H, J = 7 Hz), 6.12-6.16 (m, 2H), 6.27 (d, 1H, J = 4 Hz), 6.67 (s, 1H), 6.74 (s, 1H), 7.06-7.09 (m, 2H), 7.36-7.40 (m, 3H), 7.49 (d, 1H, J = 2 Hz), 7.87 (d, 1H, J = 9 Hz), 11.59 (s, 1H), 12.02 (s, 1H), 12.04 (s, 1H) | 702.6 (702.1) |

TABLE 1-continued

| Example | structure | Procedure[1] | $^1$H NMR (500 MHz, DMSO-d$_6$) | MS M + 1 found (calcd) |
|---|---|---|---|---|
| 58 | 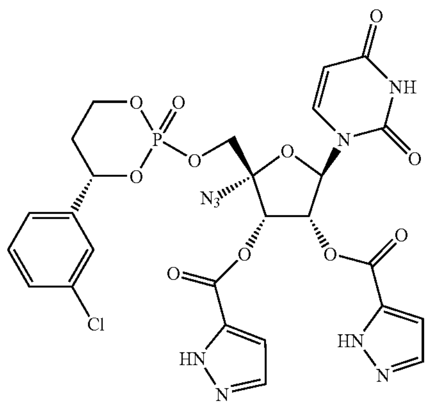 | C | δ 2.16-2.28 (m, 2H), 4.41-4.46 (m, 3H), 4.51-4.55 (m, 2H), 5.68-5.75 (m, 2H), 5.93-5.95 (m, 1H), 6.02 (d, 1H, J = 7 Hz), 6.28 (d, 1H, J = 3 Hz), 6.64 (s, 2H), 7.37-7.42 (m, 3H), 7.49 (s, 1H), 7.82 (s, 1H), 7.88 (d, 1H, J = 8 Hz), 11.60 (s, 1H), 13.55-13.65 (m, 2H) | 704.6 (704.1) |
| 59 | 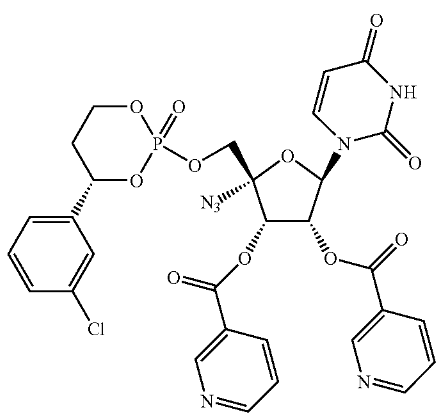 | C | δ 2.16-2.25 (m, 2H), 4.39-4.43 (m, 1H), 4.49-4.54 (m, 2H), 5.70-5.73 (m, 2H), 6.05 (dd, 1H, J = 10, 3 Hz), 6.18 (d, 1H, J = 8 Hz), 6.39 (d, 1H, J = 3 Hz), 7.33-7.35 (m, 1H), 7.38-7.39 (m, 2H), 7.46 (s, 1H), 7.49-7.52 (m, 1H), 7.54-7.57 (m, 1H), 7.83 (d, 1H, J = 8 Hz), 8.19-8.22 (m, 2H), 8.78-8.81 (m, 1H), 8.81-8.82 (m, 1H), 8.99 (d, 1H, J = 3 Hz), 9.02 (d, 1H, J = 2 Hz), 11.63 (s, 1H) | 726.4 (726.1) |
| 60 | 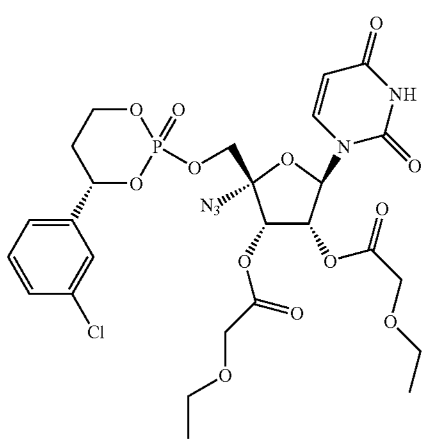 | C | δ 1.09-1.13 (m, 6H), 2.21-2.25 (m, 2H), 3.46-3.53 (m, 4H), 4.06-4.17 (m, 4H), 4.39-4.40 (m, 3H), 4.54-4.56 (m, 1H), 5.66-5.70 (m, 2H), 5.74 (d, 1H, J = 11 Hz), 5.79 (d, 1H, J = 7 Hz), 6.08 (d, 1H, J = 3 Hz), 7.37-7.44 (m, 3H), 7.49 (s, 1H), 7.79 (d, 1H, J = 8 Hz), 11.57 (s, 1H) | 688.9 (688.1) |

TABLE 1-continued

| Example | structure | Procedure[1] | $^1$H NMR (500 MHz, DMSO-$d_6$) | MS M + 1 found (calcd) |
|---|---|---|---|---|
| 61 | 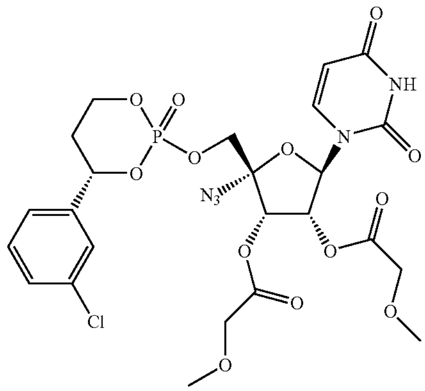 | C | δ 2.19-2.35 (m, 2H), 3.28-3.33 (m, 6H), 4.07-4.13 (m, 4H), 4.38-4.48 (m, 3H), 4.52-4.59 (m, 1H), 5.63-5.78 (m, 3H), 5.82 (d, 1H, J = 8 Hz), 6.10 (d, 1H, J = 1 Hz), 7.38-7.44 (m, 3H), 7.50 (s, 1H), 7.80 (d, 1H, J = 8 Hz), 11.59 (s, 1H) | 660.6 (660.1) |
| 62 | 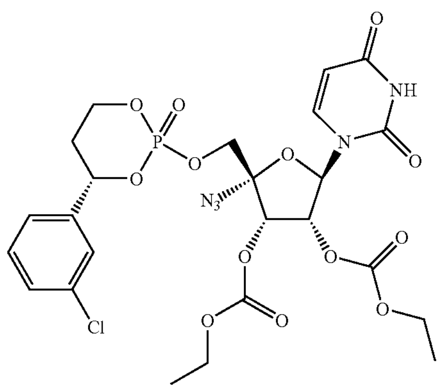 | D | δ 1.22 (t, 3H, J = 7 Hz), 1.23 (t, 3H, J = 7 Hz), 2.19-2.28 (m, 2H), 4.11-4.20 (m, 4H), 4.40-4.57 (m, 3H), 4.54-4.57 (m, 1H), 5.57 (dd, 1H, J = 7, 4 Hz), 5.66 (d, 1H, J = 7 Hz), 5.69 (dd, 2H, 7, 2 Hz), 5.75 (d, 1H, J = 10 Hz), 6.14 (d, 1H, J = 4 Hz), 7.38-7.46 (m, 3H), 7.49 (s, 1H), 7.82 (d, 1H, J = 8 Hz), 11.58 (s, 1H) | 660.6 (660.1) |
| 63 | 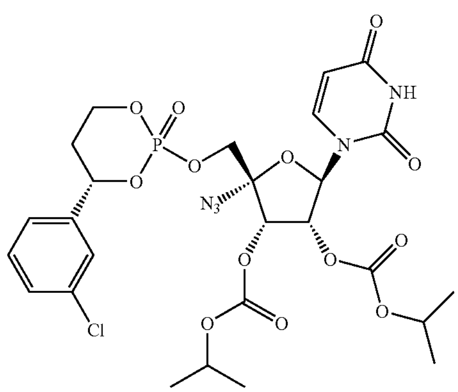 | D | δ 1.21-1.25 (m, 12H), 2.19-2.28 (m, 2H), 4.41 (d, 2H, J = 6 Hz), 4.43-4.46 (m, 1H), 4.54-4.57 (m, 1H), 4.74-4.80 (m, 2H), 5.56 (dd, 1H, J = 7, 4 Hz), 5.64 (d, 1H, J = 7 Hz), 5.69 (d, 1H, 8 Hz), 5.75 (d, 1H, J = 10 Hz), 6.14 (d, 1H, J = 3 Hz), 7.38-7.45 (m, 3H), 7.49 (s, 1H), 7.83 (d, 1H, J = 8 Hz), 11.58 (s, 1H) | 688.6 (688.1) |

[1]Methods of Preparation—Method a: See preparation of Example 10 in text; Method A: Applying Step B of Example 1 and then Step C of Example 2 to appropriate starting materials; Method B: Applying the method described in Example 3 to appropriate starting materials; Method C: Applying the method described in Example 4 to appropriate starting materials; Method D: Applying the method described in Example 6 to appropriate starting materials.

Methods of Synthesis

The compounds of this invention wherein B is uracil may be readily prepared as shown in SCHEME 1. The preparation of 4'-azidouridine (1) is described in WO 05/000864. Conversion of compound 1 to its 2',3'-O-isopropylidene derivative 0.2 enables selective phosphorylation using reagent 5 (as described in WO 07/022,073), affording 3. Mild aqueous hydrolysis of the isopropylidene group then affords compound 4. Compound 4 may be further functionalized at the 2' and 3' positions by treatment with carbonyldiimidazole (CDI to afford 6 or by esterification of the 2' and/or 3' hydroxy groups to afford 7 (as described in WO 07/022,073). Compounds wherein B is B-2, Y is O or NH and $R_3$ is $C_1$-$C_6$ alkyl may be prepared from 5'-protected 2, as described earlier in the literature (Yoshimura et al., *Org. Lett.* 2004, 6:1793-1795) or by many other known C4-pyrimidine substitution reactions.

The preparation of 4'-C-azido-2',3'-O-(1-methylethylidene)-adenosine (8, CASRN 1048373-05-2) has been described Aug. 21, 2008 by J. M. Chen et al. in WO2008/100447 A2. Conversion of 8 to the phosphate ester is accomplished by phosphorylation a 2-(4-nitro-phenoxy)-4-(hetero) aryl-[1,3,2]dioxaphosphinane 2-oxide, acid-catalyzed deketalization and acylation in analogous manner to the preparation of pyrimidine derivatives described in more detail in examples 1 to 6.

While the examples that follow describe specific acylation procedures, one skilled in the art will appreciate many variations are well known and can be adapted to the present compounds. Acylations can be conveniently carried out with a corresponding acyl halide or acid anhydride, which are prepared from the corresponding carboxylic acid, in a solvent such as $CH_2Cl_2$, $CHCl_3$, $CCl_4$, $Et_2O$, THF, dioxane, benzene, toluene, MeCN, DMF, water or sulfolane optionally in the presence of an inorganic or organic base. Typical organic bases include tertiary amines including but are not limited to pyridine, picoline, DMAP, triethylamine ($Et_3N$), tributylamine, diisopropylethylamine (DIPEA), N-methylmorphorine (NMM) and N-methylpiperidine. Typical inorganic bases include but are not limited to $K_2CO_3$, $Na_2CO_3$ and $NaHCO_3$.

Alternatively, an esters can be prepared by the coupling reaction of an alcohol with an acid in the presence or absence of a coupling reagent, e.g. diimides (e.g., 1-(3-dimethylaminopropyl)-3-ethylcarbodiimide hydrochloride, dicyclohexylcarbodiinide, 2-ethoxy-N-ethoxycarbonyl-1,2-dihydroquinoline, benzotriazol-1-yloxy-tris(dimethylamino) phosphonium hexafluorophosphate (BOP), diethyl azodicarboxylate-triphenylphosphine, diethylcyanophosphate, diethylphosphorylazide, 2-chloro-1-methylpyridinium iodide, or ethyl chloroformate, in an inert solvent, e.g. acetone, dimethylformamide, acetonitrile; halogenated hydrocarbons, such as dichloromethane, dichloroethane, chloroform; and ethers, such as tetrahydrofuran and dioxane. If desired, this reaction may be carried out in the presence of an additive such as 1-hydroxybenzotriazole or 1-hydroxyazabenzotriazole or in the presence of a base such as N-methylmorpholine. Identification of suitable conditions can readily be accomplished by one skilled in the art.

SCHEME 1

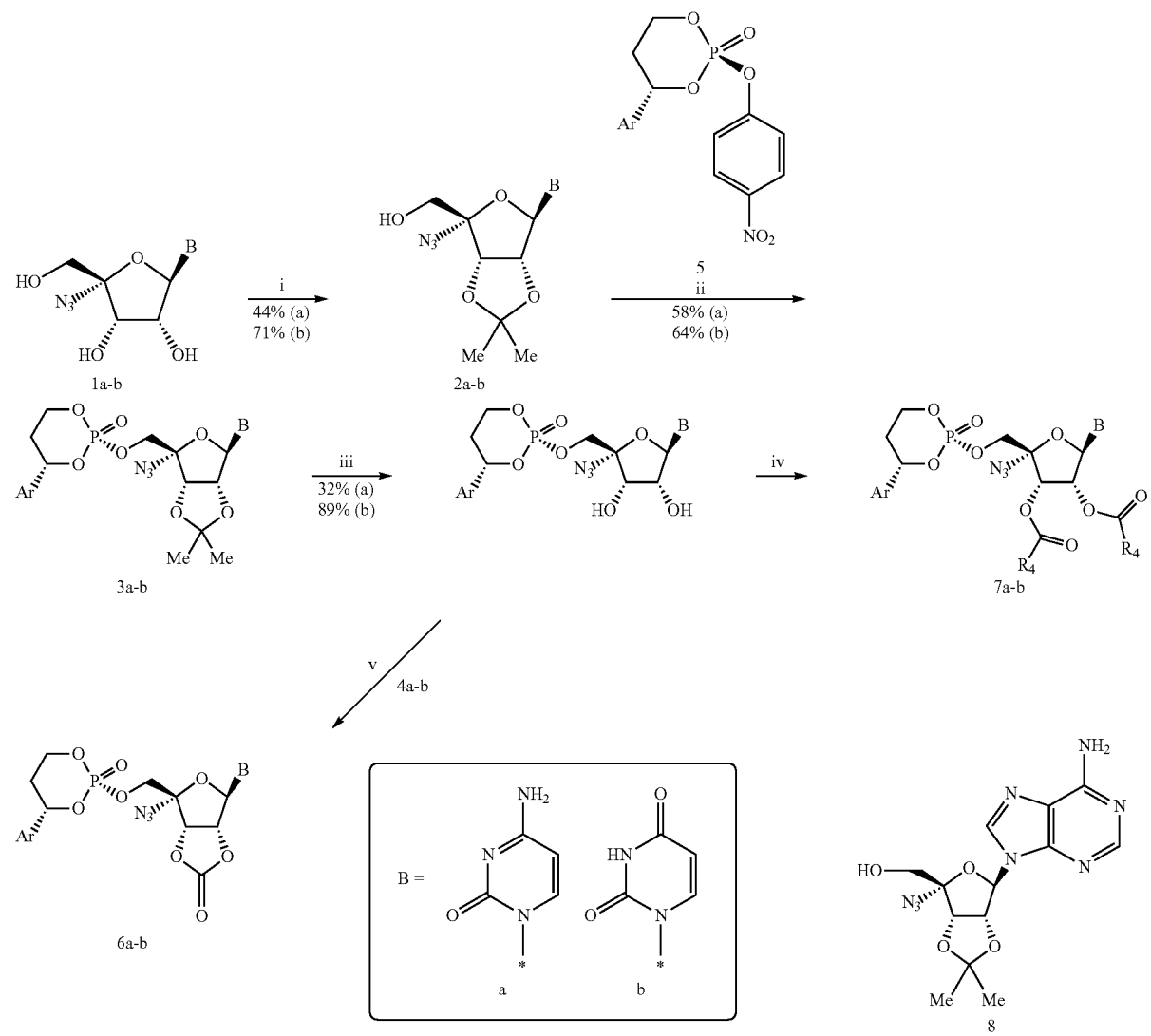

Reagents, conditions: (i) 2,2-dimethoxypropane, acetone-DMF (1:1), p-TSA, 16 H, (ii) tert-BuMgCl, DMF, 18 H, (iii) aq HCl, MeOH, (iv) (a) $R_4CO_2H$, EDCI, DMAP, DMF, or (b) $R_4COCl$, DMAP, $CH_2Cl_2$, or (c) $(R_4CO)_2O$, DIPEA, DMAP, $CH_2Cl$, (v) 1,1-carbonyldiimidazole, THF O-Alkylated uridines compounds encompassed by the present invention can be prepared by alkylation of a protected uracil derivative as depicted in SCHEME 2. One skilled in the art will appreciate that while SCHEME 2 and example the which follows utilize silyl ethers as hydroxy protecting groups, other protecting groups can be also be utilized. Step ii of SCHEME 2 can be applied to 2',3'-O-diesters (R=acyl group) to provide additional 4-O-acyl products.

SCHEME 2

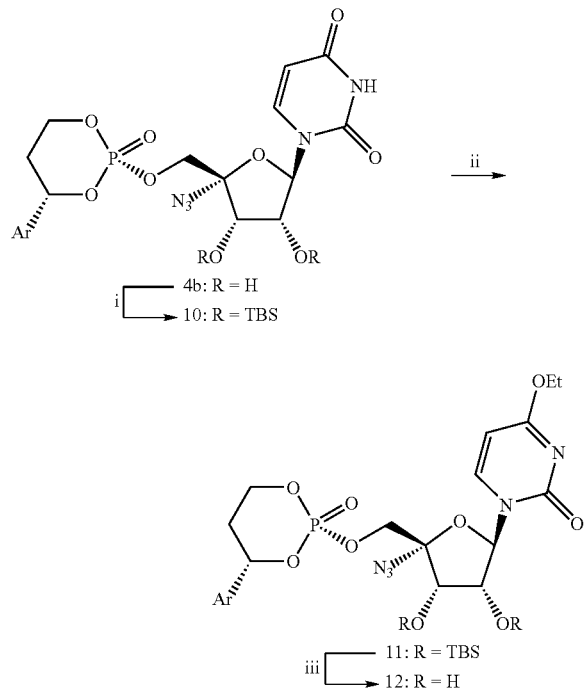

Reagents, Conditions: (i) TBSCl, imidazole, DMF; (ii) (a) p-TsCl, NMM, Et$_3$N, CH$_2$Cl$_2$; (b) EtOH, Et$_3$N; (iii) Et$_4$NF, THF
TBS = tert-Bu(Me)$_2$Si Treating rat heptocycles with cyclic 5' phosphate derivatives, exemplified by compound A and compound B, results in a dose dependent increase in nucleoside triphosphate levels with both cytosine- and uracil substituted ribosyl nucleosides. When A and B were administered to a rat by i.v. administration the cytosine substituted ribosyl phosphate A exhibited very low levels of NTP levels compared to the parent nucleoside. The uracil substituted ribosyl phosphate produced elevated levels of the corresponding triphosphate.

Compound A

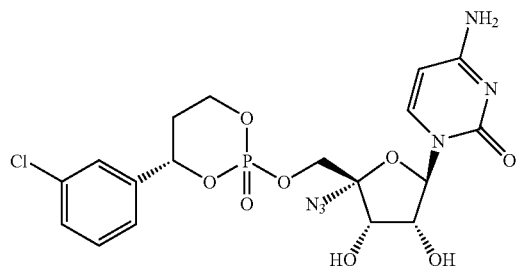

Compound B

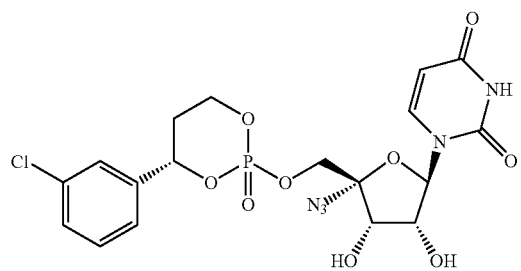

TABLE 2

| | Rat hepatocyte NTP (nmol/g @ conc.) | | Liver NTP @ 3 h (i.p. dosing, nmol/g) | | Liver NTP @ 3 h (p.o. dosing, nmol/g) | |
|---|---|---|---|---|---|---|
| | 10 µM | 100 µM | dose (mg/kg) | [NTP] | dose (mg/kg) | [NTP] |
| R1479 | <LOQ | 1.0 | 4 | 0.04 | 8 | 0.00 |
| Compound A | 36.0 | 164.0 | 5 | 0.04 | 10 | 0.19 |
| 4'-azidouridine | <LOQ | 0.2 | 5 | 0.10 | 10 | 0.00 |
| Compound B | 123.5 | 374.3 | 4 | 24.5 | 8 | 1.58 |

The low levels of nucleoside triphosphate observed in the liver after oral administration is problematical since i.v. dosing is undesirable for a compound administered overextended time periods. This poses additional problems where high levels of the antiviral agent must be maintained to repress selection of resistant strains. It has now been discovered that acylation of the ribonucleoside results in elevated absorption through the gut and the affords high levels of the phosphorylated nucleoside in the portal circulation which can be absorbed by the liver and converted to triphosphates.

Pharmacokinetic analysis of the esters was carried out as described in Example 2. The calculated value for % $F_{hepatic}$ is the ratio of measured of the quantity present in the post-hepatic $$\% \ F_{hepatic} = \frac{AUC_{jugular}}{AUC_{portal}} \times 100$$

circulation (AUC$_{jugular}$) to the pre-hepatic concentration (AUC$_{portal}$). This value reflects uptake of the prodrug by hepatocytes. Hepatocyte-targeted compounds would be expected to exhibit a AUC$_{jugular}$ value which is significantly smaller than the AUC$_{portal}$. These values reflect observed concentrations of non-esterified drug phosphate 26a. The calculated value % $F_{gut}$ is the ratio of the concentration $$\% \ F_{gut} = \frac{AUC_{p.o.,portal}}{AUC_{i.v.,jugular}} \times 100$$

of 26a observed in the portal vein which directly reflects absorption through the gut compared to the concentration observed in the jugular vein after i.v. administration of the same dose. Increased absorption through the gut will increase the observed % $F_{gut}$.

The concentration of drug in hepatocytes after oral administration can be estimated by the following formula:

TABLE 3

$$\% F = \frac{AUC_{p.o.}}{AUC_{i.v.}} \times 100.$$

| Cpd. | Portal vein AUC$_{0\to\infty}$[1]/dose | Jugular vein AUC$_{0\to\infty}$[1]/dose | % F$_{hepatic}$ | % F$_{gut}$ | % F |
|---|---|---|---|---|---|
| B | 179 | 4.43 | 2.5 | 32.7 | 0.81 |
| 45 | 7.98 | 0.25 | 3.1 | 1.5 | 0.05 |

[1]AUC = Area Under the Curve = circulating concentration of 26a (ng * h/mL/mg/kg)

Dosing of B (5 mg/kg) and 43 (7 mg/kg) resulted in almost identical efficiency of uptake by hepatocytes as evidenced by similar % F$_{hepatic}$. During the passage through the gut the diester 43 is readily hydrolyzed to 26a and no circulating diester is observed. Thus efficient uptake of orally administered B or 43 by hepatocytes was expected and observed. The diester, surprisingly, was much more efficiently absorbed through the gut as evidenced a 22-fold increase in the % F$_{gut}$ for 43 compared to B and was efficiently converted to B and taken up by hepatocytes.

Anti-Viral Activity

The activity of the inventive compounds as inhibitors of HCV activity may be measured by any of the suitable methods known to those skilled in the art, including in vivo and in vitro assays. For example, compounds of formula I which suppress HCV by inhibition of the NS5B polymerase can determined using standard assay procedures described in Behrens et al., *EMBO J.* 1996 15:12-22, Lohmann et al., *Virology* 1998 249:108-118 and Ranjith-Kumar et al., *J. Virology* 2001 75:8615-8623.

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in Remington: The Science and Practice of Pharmacy 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

In general a therapeutically effective amount of a compound of the present invention, and optionally one or more additional antiviral agents, is an amount effective to reduce the viral load or achieve a sustained viral response to therapy. Useful indicators for a sustained response, in addition to the viral load include, but are not limited to liver fibrosis, elevation in serum transaminase levels and necroinflammatory activity in the liver. One common example, which is intended to be exemplary and not limiting, of a marker is serum alanine transminase (ALT) which is measured by standard clinical assays. In some embodiments of the invention an effective treatment regimen is one which reduces ALT levels to less than about 45 IU/mL serum.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Example 1

Preparation of 4'-azido-cis-5'-O-[4-(S)-(3-chlorophenyl)-2-oxo-1,3,2-dioxaphosphorinan-2-yl]-cytidine

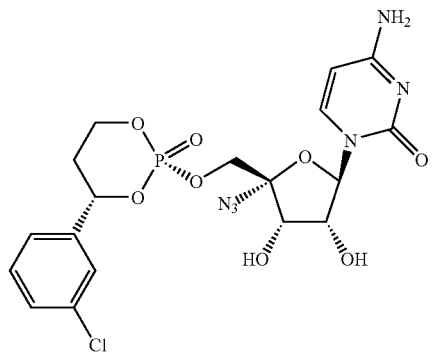

Step A: Preparation of 4'-azido-2',3'-O-isopropylidenylcytidine- To a stirred solution of 4'-azidocytidine (3.0 g, 10.56 mmol), prepared as described in WO 05000864, in a 1:1 mixture of acetone (60 mL) and N,N-dimethylformamide (60 mL), under nitrogen atmosphere, were added p-toluenesulfonic acid (6.18 g, 32.5 mmol)) followed by 2,2-dimethoxypropane (60 mL). Progress of the reaction was monitored by TLC and the reaction was neutralized with an aqueous ammonia solution upon completion after 16 h. The reaction mixture was concentrated under reduced pressure and purified by column chromatography using 8% methanol in dichloromethane to obtain the desired product (1.5 g, 44%) as a white powder.

Step B: Preparation of 4'-azido-cis-5'-O-[4-(S)-(3-chlorophenyl)-2-oxo-1,3,2-dioxaphosphorinan-2-yl]-2',3'-O-isopropylidenylcytidine- To a stirred solution of 4'-azido-2',3'-isopropylidenylcytidine (300 mg, 0.92 mmol) in THF (19 mL) under a nitrogen atmosphere was added a solution of t-butylmagnesium chloride in THF (2 M, 1.4 mL, 2.85 mmol). The reaction was allowed to stir at ambient temperature for 30 min and the phosphorylating reagent (555 mg, 1.57 mmol) was added in one portion. The reaction mixture was stirred at room temperature for 18 h (TLC). The reaction was quenched with a saturated ammonium chloride solution and extracted with EtOAc (3×25 mL). The combined extracts were washed with water and dried. The solvent was removed under reduced pressure and the residue was purified by column chromatography using 10% MeOH in dichloromethane to afford the pure phosphorylated product (300 mg, 59%).

Step C: Preparation of 4'-azido-cis-5'-O-[4-(S)-(3-chlorophenyl)-2-oxo-1,3,2-dioxaphosphorinan-2-yl]cytidine- The isopropylidenyl protected prodrug (300 mg, 0.54 mmol) was added to 90% aqueous trifluoroacetic acid solution at 0° C. The mixture was warmed to room temperature and stirred for 3 h (TLC) and concentrated upon completion. The residue was chromatographed by eluting with 10% MeOH-dichloromethane to give 120 mg (43%) of the title compound as a white solid: $^1$H NMR (500 MHz, CD$_3$OD) δ: 7.65 (d, 1H,), 7.45 (s, 1H), 7.42-7.28 (m, 4H), 6.1 (s, 1H), 5.85 (d, 1H), 5.68

(m, 2H), 4.68-4.24 (m, 4H), 2.45-2.20 (m, 2H); LC-MS calcd for $C_{18}H_{20}ClN_6O_8P$ 515.8 $(M+H)^+$; found 515.6 $(M+H)^+$.

Example 2

Preparation of 4'-azido-cis-5'-O-[4-(S)-(3-Chlorophenyl)-2-oxo-1,3,2-dioxaphosphorinan-2-yl]uridine

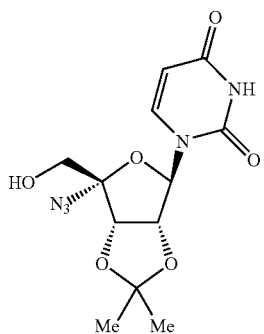

Step A: Preparation of 4'-azido-2',3'-O-isopropylidenyluridine-4'-azido-2',3'-O-isopropylidenyluridine was prepared from 4'-azidouridine (prepared as described in WO 05000864) as described in Step A of Example 1 (650 mg, 71%). TLC ($SiO_2$) Rf: 0.50 in 10% MeOH-dichloromethane;

$^1$H NMR (500 MHz, DMSO-$d_6$) δ 1.32 (s, 3H), 1.58 (s, 3H), 3.61 (dd, 1H, J=12.6 Hz), 3.64 (dd, 1H, J=12.6 Hz), 4.97 (d, 1H, J=7 Hz), 5.12 (dd, 1H, J=7.3 Hz), 5.64 (t, 1H, J=6 Hz), 5.67 (dd, 1H, J=8.1 Hz), 6.04 (d, 1H, J=2 Hz), 7.79 (d, 1H, J=8 Hz), 11.48 (s, 1H).

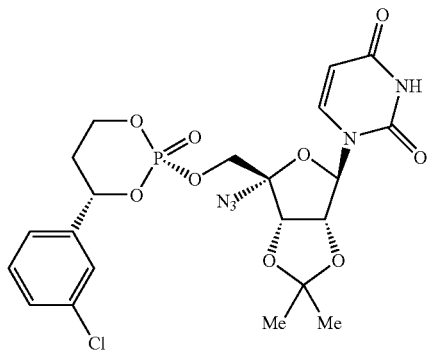

Step B: Preparation of 4'-azido-cis-5'-O-[4-(S)-(3-chlorophenyl)-2-oxo-1,3,2-dioxaphosphorinan-2-yl]-2',3'-O-isopropylidenyluridine- The prodrug formation of 2',3'-isopropylidinyl-4'-azidouridine was done as described in Step B of Example 1 (110 mg, 64%). $^1$H NMR (500 MHz, DMSO-$d_6$) δ 1.33 (s, 3H), 1.60 (s, 3H), 2.16-2.30 (m, 2H), 4.31 (d, 2H, J=7 Hz), 4.38-4.45 (m, 1H), 4.51-4.57 (m, 1H), 5.04 (d, 1H, J=7 Hz), 5.28 (dd, 1H, J=7.2 Hz), 5.65 (d, 1H, 8 Hz), 5.74 (dt, 1H, J=11.3 Hz), 6.05 (d, 1H, J=2 Hz), 7.40-7.47 (m, 3H), 7.52 (s, 1H), 7.82 (d, 1H, J=8 Hz), 11.54 (s, 1H).

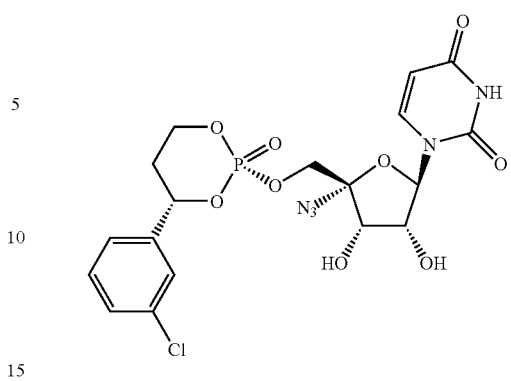

Step C: Preparation of 4'-azido-cis-5'-O-[4-(S)-(3-chlorophenyl)-2-oxo-1,3,2-dioxaphosphorinan-2-yl]uridine The product of Step B (1.00 g, 1.8 mmol) was stirred in 5 mL methanol and 0.75 mL of conc. HCl (9.0 mmol) at rt for 16 h. The solution was diluted with EtOAc, washed with sat'd aqueous $NaHCO_3$. The layers separated and the aqueous layer extracted with EtOAc and combined organic layers dried ($MgSO_4$) and evaporated to provide 0.83 μg (89%) of the title compound as an amorphous white solid: $^1$H NMR (500 MHz, DMSO-$d_6$) δ 2.16-2.30 (m, 2H), 4.12-4.25 (m, 3H), 4.38 (q, 1H, J=6 Hz), 4.4-4.5 (m, 1H), 4.53-4.6 (m, 1H), 5.62 (d, 1H, J=8 Hz), 5.72-5.75 (m, 2H), 6.07 (d, 2H, J=6 Hz), 7.40-7.45 (m, 3H), 7.53 (s, 1H), 7.70 (d, 1H, J=8 Hz), 11.48 (s, 1H); LC-MS: calculated for $C_{18}H_{19}ClN_5O_9P$ 516.1 $(M+H)^+$, observed m/e 516.6 $(M+H)^+$.

Example 3

Preparation of 2',3'-O-bis-acetyl-4'-azido-cis-5'-O-[4-(S)-(3-chlorophenyl)-2-oxo-1,3,2-dioxaphosphorinan-2-yl]uridine

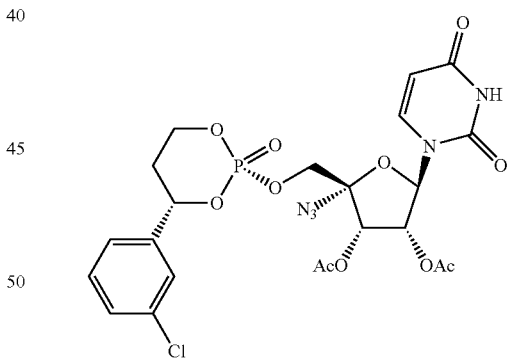

To a solution of 4'-azido-cis-5'-O-[4-(S)-(3-chlorophenyl)-2-oxo-1,3,2-dioxaphosphorinan-2-yl]uridine (Example 2) (502 mg, 0.973 mmol) in THF (5.0 mL) at 0° C. was added N,N-diisopropylethylamine (1.29 mL, 7.81 mmol) and 4-dimethylaminopyridine (61.3 mg, 0.502 mmol), followed by acetic anhydride (0.55 mL, 5.82 mmol). The reaction mixture was stirred at room temperature for 60 min, then diluted with aqueous saturated sodium bicarbonate (20 mL) and extracted with ethyl acetate (2×20 mL). The organic layer was rinsed with water (20 mL) and brine (20 mL), dried ($Na_2SO_4$), and evaporated. The crude product was purified by column chromatography on silica gel, eluted with dichloromethane-methanol (97:3) to afford 360 mg (88%) of the title compound as a white solid: $^1$H NMR (500 MHz, DMSO-$d_6$) δ 2.06 (s, 3H.) 2.09 (s, 3H), 2.26 (m, 2H), 4.37 (d, 2H, J=6.5 Hz), 4.54 (m, 1H), 4.55 (m, 1H), 5.59 (m, 1H), 5.66 (d, 1H, J=8 Hz), 5.68 (d, 1H, J=6.5 Hz), 5.74 (dd, 1H, J=4.5, 3.5 Hz), 6.08 (s, 1H), 7.37 (d, 1H, J=2 Hz), 7.43 (m, 2H), 7.49 (s, 1H), 7.79 (d, 1H, J=8 Hz), 11.56 (s, 1H); LC-MS: calculated for $C_{22}H_{23}ClN_5O_{11}P$: 600.1 $(M+H)^+$, observed m/e 600.9 $(M+H)^+$.

Example 4

Preparation of 4'-Azido-cis-5'-O-[4-(S)-(3-chlorophenyl)-2-oxo-1,3,2-dioxaphosphorinan-2-yl]-2',3'-O-bis-(3-methoxypropionyl)uridine

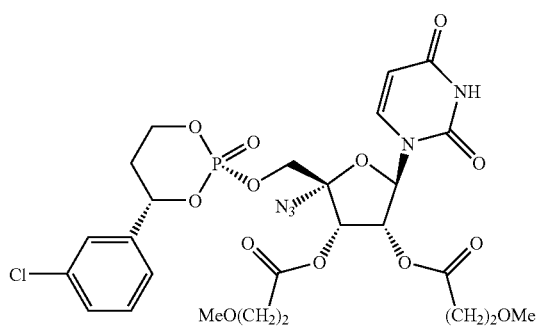

A mixture of 4'-azido-cis-5'-O-[4-(S)-(3-chlorophenyl)-2-oxo-1,3,2-dioxaphosphorinan-2-yl]uridine (Example 2) (96 mg, 0.19 mmol), 3-methoxypropionic acid (0.069 mL, 0.74 mmol), EDCI (142 mg, 0.74 mmol) and DMAP (90 mg, 0.74 mmol) in 1 mL of DMF was stirred at rt for 4 h, diluted with EtOAc, washed with 5% aqueous HCl, water, saturated aqueous NaHCO$_3$, brine, dried (MgSO$_4$) and evaporated. The residue was subjected to chromatography on SiO$_2$ and eluted with 66-90% EtOAc in hexanes (20 min ramp) to provide 62 mg (47%) of the title compound as a white solid: $^1$H NMR (500 MHz, DMSO-$d_6$) δ 2.21-2.28 (m, 2H), 2.60-2.63 (m, 4H), 3.21 (s, 6H), 3.54-3.56 (m, 4H), 4.36 (d, 2H, J=6.5 Hz), 4.37-4.44 (m, 1H), 4.54-4.56 (m, 1H), 5.63-5.73 (m, 2H), 5.74-5.76 (m, 2H), 6.08 (s, 1H), 7.37 (d, 1H, J=8 Hz), 7.42-7.44 (m, 2H), 7.50 (s, 1H), 7.78 (d, 1H, J=8 Hz), 11.57 (s, 1H); LC-MS: calculated for $C_{26}H_{31}ClN_5O_{13}P$ 688.1 $(M+H)^+$, observed m/e 688.9 $(M+H)^+$.

Example 5

Preparation of 4'-azido-2',3'-O-carbonyl-cis-5'-O-[4-(S)-(3-chlorophenyl)-2-oxo-1,3,2-dioxaphosphorinan-2-yl]uridine

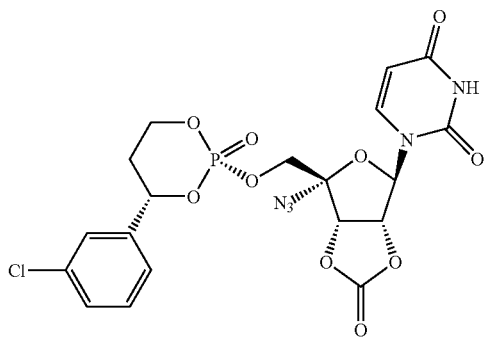

To a solution of 4'-azido-cis-5'-O-[4-(S)-(3-chlorophenyl)-2-oxo-1,3,2-dioxaphosphorinan-2-yl]uridine (Example 2) (823 mg, 1.60 mmol) in THF (8.2 mL) was added 1,1-carbonyldiimidazole (781 mg, 4.82 mmol). The reaction mixture was stirred at room temperature for 16 h, then diluted with water (20 mL) and extracted with ethyl acetate (2×20 mL). The organic layer was washed with water, brine, dried (Na$_2$SO$_4$) and evaporated. The residue was purified by column chromatography on silica gel eluted with ethyl acetate to afford 261 mg (30%) of the title compound as a white solid: $^1$H NMR (500 MHz, DMSO-$d_6$) δ 2.19-2.32 (m, 2H), 4.39-4.59 (m, 4H), 5.50 (d, 1H, J=7.5 Hz), 5.67 (d, 1H, J=8 Hz), 5.74-5.77 (m, 2H), 6.30 (s, 1H), 7.39-7.47 (m, 3H), 7.50 (s, 1H), 7.78 (d, 1H, J=8 Hz), 11.63 (s, 1H); LC-MS: calculated for $C_{19}H_{17}ClN_5O_{10}P$ 542.0 $(M+H)^+$, observed m/e 542.6 $(M+H)^+$.

Example 6

Preparation of 4'-azido-cis-5'-O-[4-(S)-(3-chlorophenyl)-2-oxo-1,3,2-dioxaphosphorinan-2-yl]uridine 2',3'-O-bis-(methoxycarbonate)

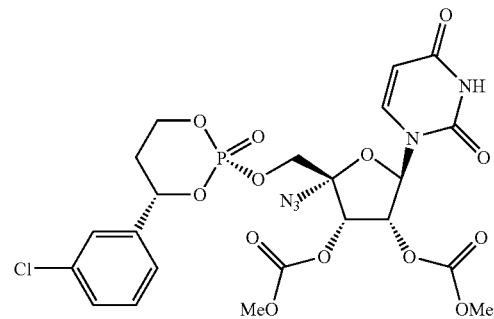

To a solution of 4'-azido-cis-5'-O-[4-(S)-(3-chlorophenyl)-2-oxo-1,3,2-dioxaphosphorinan-2-yl]uridine (Example 2) (500 mg, 0.97 mmol) and DMAP (293 mg, 2.4 mmol) in 5 mL of CH$_2$Cl$_2$ at 0° C. was added methyl chloroformate (0.19 mL, 2.4 mmol) and the resulting solution stirred for 1 h at rt, diluted with CH$_2$Cl$_2$ and washed with 5% aqueous HCl, brine, dried (MgSO$_4$) and concentrated by evaporation under reduced pressure which resulted in precipitation of the title compound, 322 mg (53% as a white solid: $^1$H NMR (500 MHz, DMSO-$d_6$) δ 2.19-2.28 (m, 2H), 3.74 (s, 6H), 4.37-4.47 (m, 2H), 4.53-4.57 (m, 1H), 5.57 (dd, 1H, J=7.4 Hz), 5.67 (d, 1H, J=7 Hz), 5.69 (dd, 2H, 9.3 Hz), 5.75 (d, 1H, J=11 Hz), 6.14 (d, 1H, J=3 Hz), 7.38-7.46 (m, 3H), 7.49 (s, 1H), 7.80 (d, 1H, J=8 Hz), 11.59 (s, 1H); LC-MS: calculated for $C_{22}H_{23}ClN_5O_{13}P$ 632.1 $(M+H)^+$, observed m/e 632.6 $(M+H)^+$.

Example 7

Preparation of 4'-Azido-cis-5'-O-[4-(S)-(3-chlorophenyl)-2-oxo-1,3,2-dioxaphosphorinan-2-yl]uridine 2',3'-O-bis-(tert-butoxycarbonate)

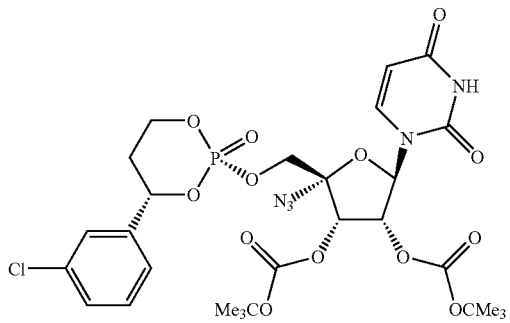

To a solution of 4'-azido-cis-5'-O-[4-(S)-(3-chlorophenyl)-2-oxo-1,3,2-dioxaphosphorinan-2-yl]uridine (Example 2) (600 mg, 1.16 mmol) and DMAP (285 mg, 2.33 mmol) in 6 mL of CH$_2$Cl$_2$ at −20° C. was added di-t-butyl dicarbonate (0.53 mL, 2.33 mmol) and the mixture stirred for 2 h at −20° C. Then it was diluted with CH$_2$Cl$_2$ and washed with 5% aqueous HCl, brine, dried (MgSO$_4$) and evaporated. The residue was subjected to chromatography on SiO$_2$ and eluted with 50-75% EtOAc in hexanes (20 min ramp) to provide 544 mg (65%) of the title compound as a white solid: $^1$H NMR (500 MHz, DMSO-d$_6$) δ 1.41 (s, 9H), 1.42 (s, 9H), 2.19-2.28 (m, 2H), 4.37-4.47 (m, 3H), 4.53-4.57 (m, 1H), 5.51 (dd, 1H, J=7.4 Hz), 5.58 (d, 1H, J=8 Hz), 5.68 (dd, 2H, J=8.3 Hz), 5.75 (d, 1H, J=10 Hz), 6.12 (d, 1H, J=4 Hz), 7.38-7.45 (m, 3H), 7.45 (s, 1H), 7.83 (d, 1H, J=8 Hz), 11.57 (d, 1H, J=2 Hz); LC-MS: calculated for C$_{28}$H$_{35}$ClN$_5$O$_{13}$P 716.2 (M+H)$^+$, observed m/e 716.9 (M+H)$^+$.

Example 8

Preparation of 1,1-Dimethylethyl 1,2-dihydro-2-oxo-1-{4-azido-cis-5-O-[4-(S)-(3-chlorophenyl)-2-oxo-1,3,2-dioxaphosphorinan-2-yl]-2,3-bis-(t-butoxycarbonyl)-β-ribofuranosyl}-4-pyrimidinyl carbonate

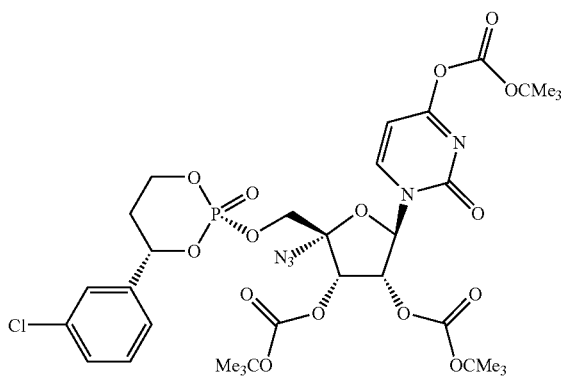

To a solution of 4'-azido-cis-5'-O-[4-(S)-(3-chlorophenyl)-2-oxo-1,3,2-dioxaphosphorinan-2-yl]uridine (Example 2), (500 mg, 0.97 mmol), DIEA (0.99 mL, 5.82 mmol) and DMAP (119 mg, 0.97 mmol) in 5 mL of CH$_2$Cl$_2$ at 0° C. was added di-t-butyl dicarbonate (1.32 mL, 5.82 mmol) and the mixture stirred for 72 h at rt. Then it was diluted with CH$_2$Cl$_2$ and washed with 5% aqueous HCl, brine, dried (MgSO$_4$) and evaporated. The residue was subjected to chromatography on SiO$_2$ and eluted with 20-33% acetone in hexanes (20 min ramp) to provide 231 mg (29%) of the title compound as a white solid: $^1$H NMR (500 MHz, DMSO-d$_6$) δ 1.41 (s, 9H), 1.43 (s, 9H), 1.51 (s, 9H), 2.19-2.28 (m, 2H), 4.37-4.47 (m, 3H), 4.53-4.60 (m, 1H), 5.54 (s, 1H), 5.76 (d, 1H, J=10 Hz), 5.91 (d, 2H, J=9 Hz), 6.16 (s, 1H), 7.38-7.43 (m, 3H), 7.50 (s, 1H), 7.96 (d, 1H, J=8 Hz); LC-MS: calculated for C$_{33}$H$_{43}$ClN$_5$O$_{15}$P 816.2 (M+H)$^+$, observed m/e 816.9 (M+H)$^+$.

Example 9

Preparation of 1,2-dihydro-2-oxo-1-{4-azido-cis-5-O-[4-(S)-(3-chlorophenyl)-2-oxo-1,3,2-dioxaphosphorinan-2-yl]-β-D-ribofuranosyl}-4-ethoxypyrimidine

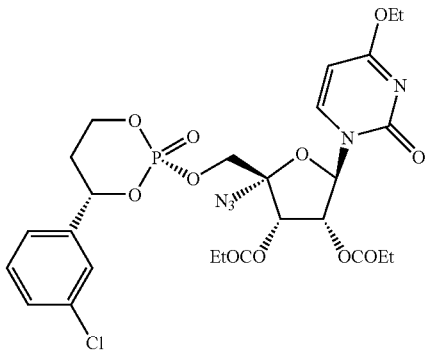

Step A A mixture of 4'-azido-cis-5'-O-[4-(S)-(3-chlorophenyl)-2-oxo-1,3,2-dioxaphosphorinan-2-yl]uridine 2',3'-O-bis-propionate (see Example 45 in Table 1, 1.00 g, 1.6 mmol), Et$_3$N (0.55 mL, 4.0 mmol), N-methylmorpholine (0.53 mL, 4.8 mmol) and p-toluenesulfonyl chloride (488 mg, 2.4 nmol) was stirred in 20 mL CH$_2$Cl$_2$ for 1 h at rt. Then 4 mL of ethanol and Et$_3$N (2.2 mL, 16 mmol) was added and the mixture stirred for 16 h at rt. Then the solvent was evaporated, the residue diluted with EtOAc, washed with water, dried (Na$_2$SO$_4$) and evaporated. The residue was subjected to chromatography on SiO$_2$ and eluted with hexane/EtOAc to provide 0.10 g (10%) of the title compound as a white solid: $^1$H NMR (300 MHz, DMSO-d$_6$) δ 1.02 (t, 3H, J=7 Hz), 1.03 (t, 3H, J=7 Hz), 1.27 (t, 3H, J=7 Hz), 2.2-2.4 (m, 4H), 4.28 (q, 2H, J=7 Hz), 4.37 (d, 2H, J=7 Hz), 4.4-4.6 (m, 3H), 5.62 (dd, 1H, J=7.3 Hz), 5.72 (dt, 1H, J=11.3 Hz), 6.06 (d, 1H, J=8 Hz), 6.08 (d, 1H, J=4 Hz), 7.3-7.4 (m, 3H), 7.47 (s, 1H), 8.06 (d, 1H, J=8 Hz); LC-MS: calculated for C$_{26}$H$_{31}$ClN$_5$O$_{11}$P 656.1 (M+H)$^+$, observed m/e 656.6 (M+H)$^+$.

Example 10

Preparation of 4'-azido-cis-5'-O-[4-(S)-(3-chlorophenyl)-2-oxo-1,3,2-dioxaphosphorinan-2-yl]-2',3'-O-bis-propionate-adenosine

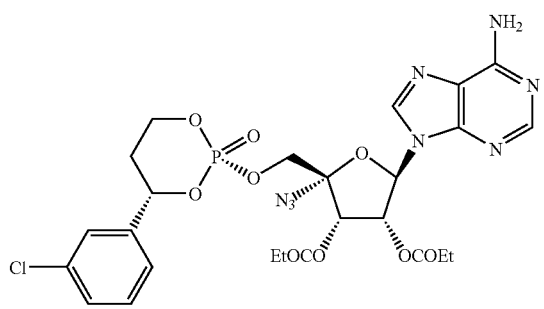

The title compound is prepared as described in Example 1, Steps A-C, from 9-{6-azido-6-[4-(3-chloro-phenyl)-2-oxo-2-$\lambda^5$-[1,3,2]dioxaphosphinan-2-yloxymethyl]-2,2-dimethyl-tetrahydro-furo[3,4-d][1,3]dioxol-4-yl}-9H-purin-6-ylamine (prepared as described by J. M. Chen et al. in WO2008/100447 A2). Acylation of the hydroxyl groups can be carried out with the desired acid as described in, e.g., example 4

Example 11

NTP Generation in Rat Hepatocytes

Hepatocytes were prepared from male Wistar rats (250-300 g) according to the procedure of Berry and Friend (Berry, M. N.; Friend, D. S. J. Cell Biol. 1969, 43, 506-520) as modified by Groen (Groen, A. K.; Sips, H. J.; Vervoom, R. C.; Tager, J. M. Eur. J. Biochem. 1982, 122, 87-93). Hepatocytes (20 mg/mL wet weight, >85% trypan blue viability) were incubated at 37° C. in 2 mL of Krebs-bicarbonate buffer containing 20 mM glucose, and 1 mg/mL BSA for 2 h in the presence of 10 μM nucleoside or prodrug (from 10 mM stock solutions in DMSO, n>4).

Following the incubation of 4'-azidocytidine analogues, 1600 μL aliquot of the cell suspension was centrifuged and 300 μL of acetonitrile was added to the pellet, vortexed and sonicated until the pellet broke down. Then 200 μL of water was added to make a 60% acetonitrile solution. After 10 min centrifugation at 14,000 rpm, the resulting supernatant was transferred to a new vial and evaporated to near dryness in a Savant SpeedVac Plus at room temperature. The dried residue was reconstituted with 200 μL of water and the mixture was centrifuged for 10 min at 14,000 rpm. A mixture of 35 μL aliquot of supernatant and 35 μL of mobile phase A (20 mM N—N-dimethylhexylamine and 10 mM propionic acid in 20% methanol) was analyzed by LC-MS/MS (Applied Biosystems, API 4000) equipped with an Agilent 1100 binary pump and a LEAP injector. NTP was detected by using MS/MS mode (M-/78.8) and quantified based on comparison to a standard of 2'-C-methyladenosine-5'-triphosphate for 4'-azidocytidine and the compound described in Example 1.

Following incubation of the 4'-azidouridine analogues, 1600 μL aliquot of the cell suspension was centrifuged and 500 μL of acetonitrile containing 0.1 mg/mL dicyclohexyl-carbodiimide (DCCD) and 0.1% ammonium hydroxide was added to the pellet and vigorously mixed by vortexing. Liver extracts were analyzed by LC-MS/MS using a Luna NH$_2$ column (5 micron, 2×50 mm, Phenomenex) fitted with a SecurityGuard C18 guard column (5 micron, 4.0×2.0 mm, Phenomenex) and eluted with a gradient from mobile phase A (10 mM ammonium acetate in 50% acetonitrile) to B (1 mM ammonium acetate in 50% acetonitrile containing 1% concentrated ammonium hydroxide) at a flow rate of 0.6 mL/min. The injector temperature was set at 4° C. 4'-AUMP, 4'-AUDP, and 4'-ALTP were detected using the MS/MS mode (364.1/150.8 for 4'-AUMP, 444.1/176.8 for 4'-AUDP, and 524.1/158.9 for 4'-AUTP) and quantified by comparison of peak areas to standard curves obtained by spiking known concentrations of the analytes to blank liver extract.

Conversion of compounds to nucleoside triphosphate (NTP) in rat hepatocytes is shown in Table 4.

TABLE 4

| Example | nmol NTP/g @ 10 μM (±SEM) |
|---|---|
| 4'-AC | <LOQ |
| 1 (Compound A) | 23.4 (±16.6) |
| 4'-AU | 0.3 (±0.2) |
| 2 (Compound B) | 66.1 (±10.6) |
| 10 | 4.8 ((±0.2) |
| 11 | 47.9 (±4.8) |
| 12 | 61.7 (±3.7) |
| 13 | 52.7 (±1.6) |
| 14 | 59.5 (±2.5) |
| 15 | 6.9 (±0.8) |
| 16 | 14.4 (±3.4) |
| 17 | 19.0 (±0.5) |
| 18 | 32.5 (±0.6) |
| 19 | 41.3 (±1.9) |
| 20 | 31.3 (±0.7) |
| 21 | 19.9 (±5.6) |
| 22 | 29.3 (±5.8) |
| 23 | 61.9 (±10.9) |
| 24 | 20.3 (±4.0) |
| 25 | 46.8 (±8.5) |
| 26 | 31.9 (±5.1) |
| 27 | 55.3 (±2.9) |
| 28 | 23.0 (±1.9) |
| 29 | 59.3 (±1.6) |
| 30 | 22.1 (±8.8) |
| 31 | 23.4 (±1.4) |
| 32 | 12.2 (±0.8) |
| 33 | 75.3 (±1.8) |
| 34 | 73.2 (±9.2) |
| 35 | 24.1 (±5.6) |
| 36 | 48.0 (±7.5) |
| 37 | 16.5 (±0.8) |
| 38 | 44.5 (±9.0) |
| 39 | 29.2 (±1.1) |
| 40 | 24.3 (±1.9) |
| 41 | 3.8 (±0.6) |
| 42 | 30.0 (±2.5) |
| 43 | 23.8 (±3.6) |
| 44 | 7.7 (±0.3) |

Example 12

Evaluation of Liver NTP Levels in Rat

Nucleoside analogues and their prodrugs were administered to Sprague-Dawley or Wistar rats by oral gavage or intraperitoneal injection. At 3 or 5 h following drug administration, liver samples (~1 g) were freeze-clamped and homogenized in 10 volumes of ice-cold 70% methanol containing 20 mM EDTA/EGTA for 4'-azidocytidine analogues or 10 volumes of 60% acetonitrile in water containing 1 mg/mL dicyclohexylcarbodiimide (DCCD) and 0.1% ammonium hydroxide. Following centrifugation to clarify the homogenate, the supernatants were analyzed by LC-MS/MS as described in Example 57.

The concentration of nucleoside triphosphate in the liver 3 hours after an intraperitoneal dose of the compounds is shown in Table 3.

The concentration of nucleoside triphosphate in the liver 3 hours after an intraperitoneal dose of the compounds is shown in Table 5.

TABLE 5

| Compound | Liver NTP @ 3 hr, nmol/g (dose, nucleoside equiv.) |
|---|---|
| 4'-AC | <LOQ (4 mg/kg) |
| Compound A | <LOQ (5 mg/kg) |
| 4'-AU | <LOQ (5 mg/kg) |
| Compound B | 9.9 (3 mg/kg) |

Example 13

Protocol for Rat Portal Vein Studies

Male Hanover-Wistar (HW) rats were obtained from Charles River Laboratories (Wilmington, Mass.). Rats were received surgically modified by implantation of cannulas in the portal and jugular veins. Prodrugs were administered intravenously (IV) at 1 mg/kg and orally (PO) at 7 mg/kg (26b) or 5 mg/kg (26a) to male HW rats (n=3/group). Compounds for IV administration were formulated in 12% ethanol/15% propylene glycol/20% PEG400/53% of 5% Dextrose and the IV administration of single prodrug was formulated in saline. Formulations for oral administration were suspensions in hydroxypropyl methylcellulose (HPMC). Blood samples were simultaneously collected at various time points from the portal and jugular veins up to eight hours post-dose in tubes with sodium fluoride/potassium oxalate as anticoagulant. Plasma was immediately prepared from the blood samples by centrifugation at −20° C. Plasma samples were extracted by protein precipitation and analyzed by liquid chromatography coupled to tandem mass spectrometry (LC/MS/MS) for concentrations of 26b, 26a and 20.

Pharmacokinetic parameters were calculated using a noncompartmental model in Watson software (Watson, Thermo Fisher, Waltham, Mass.). % $F_{hepatic}$ was calculated from the dose-normalized area under the curve (AUC) values obtained from sampling either the portal or jugular vein after PO administration as follows:

$$\% \ F_{hepatic} = \frac{AUC_{jugular}}{AUC_{portal}} \times 100$$

Absolute oral bioavailability (% F) was calculated from the dose-normalized AUC values obtained after sampling the jugular vein after IV and PO administration as follows:

$$\% \ F = \frac{AUC_{p.o.}}{AUC_{i.v.}} \times 100$$

% Fgut is defined as the percentage of the orally administered dose entering the portal vein and was calculated from the dose-normalized AUC values obtained after sampling the portal vein after PO administration and sampling the jugular vein after IV administration as follows:

$$\% \ F_{gut} = \frac{AUC_{p.o.,portal}}{AUC_{i.v.,jugular}} \times 100$$

Example 14

HCV NS5B RNA Polymerase Activity

The enzymatic activity of HCV polymerase (NS5B570n-Con1) was measured as the incorporation of radiolabeled nucleotide monophosphates into acid insoluble RNA products. Unincorporated radiolabeled substrate was removed by filtration and scintillant was added to the washed and dried filter plate containing radiolabeled RNA product. The amount of RNA product generated by NS5B570-Con1 at the end of the reaction was directly proportional to the amount of light emitted by the scintillant.

The N-terminal 6-histidine tagged HCV polymerase, derived from HCV Con1 strain, genotype 1b (NS5B570n-Con1) contains a 21 amino acid deletion at the C-terminus relative to the full-length HCV polymerase and was purified from E. coli strain BL21 (DE) pLysS. The construct, containing the coding sequence of HCV NS5B Con1 (GenBank accession number AJ242654) was inserted into the plasmid construct pET17b, downstream of a T7 promoter expression cassette and transformed into E. coli. A single colony was grown overnight as a starter culture and later used inoculate 10 L of LB media supplemented with 100 μg/mL ampicillin at 37° C. Protein expression was induced by the addition of 0.25 mM isopropyl-β-D-thiogalactopyranoside (IPTG) when optical density at 600 nM of the culture was between 0.6 and 0.8 and cells were harvested after 16 to 18 h at 30° C. NS5B570n-Con1 was purified to homogeneity using a three-step protocol including subsequent column chromatography on Ni-NTA, SP-Sepharose HP and Superdex 75 resins.

Each 50 μl enzymatic reaction contained 20 nM RNA template derived from the complementary sequence of the Internal Ribosome Entry Site (cIRES), 20 nM NS5B570n-Con1 enzyme, 0.5 μCi of tritiated UTP (Perkin Elmer catalog no. TRK-412; specific activity: 30 to 60 Ci/mmol; stock solution concentration from $7.5 \times 10^{-5}$ M to $20.6 \times 10^{-6}$ M), 1 μM each ATP, CTP, and GTP, 40 mM Tris-HCl pH 8.0, 40 mM NaCl, 4 mM DTT (dithiothreitol), 4 mM MgCl2, and 5 μl of compound serial diluted in DMSO. Reaction mixtures were assembled in 96-well filter plates (cat #MADVN0B, Millipore Co.) and incubated for 2 h at 30° C. Reactions were stopped by addition of 10% final (v/v) trichloroacetic acid and incubated for 40 min at 4° C. Reactions were filtered, washed with 8 reaction volumes of 10% (v/v) trichloroacetic acetic acid, 4 reaction volumes of 70% (v/v) ethanol, air dried, and 25 μl of scintillant (Microscint 20, Perkin-Elmer) was added to each reaction well.

The amount of light emitted from the scintillant was converted to counts per minute (CPM) on a Topcount® plate reader (Perkin-Elmer, Energy Range: Low, Efficiency Mode: Normal, Count Time: 1 min, Background Subtract: none, Cross talk reduction: Off).

Data was analyzed in Excel® (Microsoft®) and Activity-Base® (Idbs®). The reaction in the absence of enzyme was used to determine the background signal, which was subtracted from the enzymatic reactions. Positive control reactions were performed in the absence of compound, from which the background corrected activity was set as 100% polymerase activity. All data was expressed as a percentage of the positive control. The compound concentration at which the enzyme-catalyzed rate of $$Y = \% \text{ Min} + \frac{(\% \text{ Max} - \% \text{ Min})}{\left[1 + \frac{X}{(IC_{50})^S}\right]} \quad (i)$$

RNA synthesis was reduced by 50% ($IC_{50}$) was calculated by fitting equation (i) to the data where "Y" corresponds to the relative enzyme activity (in %), "% Min" is the residual relative activity at saturating compound concentration, "% Max" is the relative maximum enzymatic activity, "X" corresponds to the compound concentration, and "S" is the Hill coefficient (or slope).

TABLE 6

| Compound Number | Polymerase Assay $IC_{50}$ (μM) |
|---|---|
| 4'-AU monophosphate | 0.218 |

Example 15

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound of general formula I or II

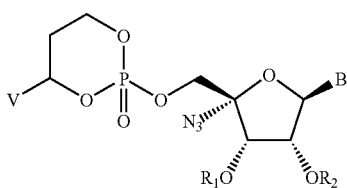

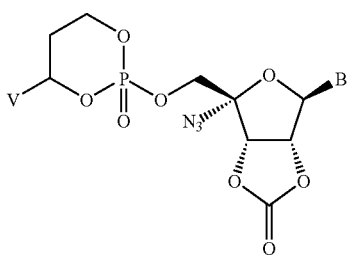

wherein V is phenyl or pyridinyl said phenyl or pyridinyl optionally substituted with one to three substituents selected from the group consisting of halogen, $C_{1-6}$ alkyl, $C_{1-6}$ haloalkyl, $C_{1-6}$ alkoxy, or cyano;

B is

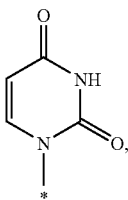

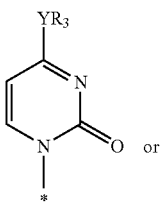

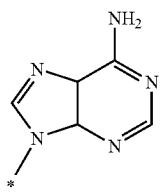

$R_1$ and $R_2$ are independently selected from H and or $COR_4$;
Y is O or NH;
$R_3$ is $C_1$-$C_6$ alkyl or $COR_4$ and,
$R_4$ is $C_{1-6}$ alkyl, $C_{1-3}$ alkoxy-$C_{1-6}$ alkyl, $C_{3-6}$ cycloalkyl, $C_{3-6}$ cycloalkyl-$C_{1-3}$ alkyl, $C_{1-6}$ alkoxy or heteroaryl wherein the heteroaryl is a five-membered ring containing one or two heteroatoms selected from nitrogen, oxygen or sulfur or pyridine or a six-membered ring with one or two nitrogen atoms; or,
a pharmaceutically acceptable salt thereof.

2. A compound according to formula I of claim 1 wherein B is B-1.

3. A compound according to claim 2 wherein V is optionally substituted phenyl, $R_1$ and $R_2$ are independently hydrogen or $COR_4$; and $R_4$ is $C_{1-6}$ alkyl.

4. A compound according to formula II of claim 1.

5. A compound according to formula II of claim 3 wherein V is optionally substituted phenyl and B is B-1.

6. A compound according to claim 1 wherein B is B-2.

7. A compound according to claim 6 wherein V is optionally substituted phenyl.

8. A compound according to claim 1 wherein B is B-3.

9. A compound according to claim 8 wherein V is optionally substituted phenyl.

10. A compound according to claim 1 selected from the group consisting of:

4'-azido-cis-5'-O-[4-(R,S)-(3-fluorophenyl)-2-oxo-1,3,2-dioxaphosphorinan-2-yl]uridine;
4'-azido-cis-5'-O-[4-(R,S)-(3-bromophenyl)-2-oxo-1,3,2-dioxaphosphorinan-2-yl]uridine;
4'-azido-cis-5'-O-[4-(R,S)-(3-bromo-4-fluorophenyl)-2-oxo-1,3,2-dioxaphosphorinan-2-yl]uridine;
4'-azido-cis-5'-O-[4-(R,S)-(3-chloro-4-fluorophenyl)-2-oxo-1,3,2-dioxaphosphorinan-2-yl]uridine;
4'-azido-cis-5'-O-[4-(R,S)-phenyl-2-oxo-1,3,2-dioxaphosphorinan-2-yl]uridine;
4'-azido-cis-5'-O-[4-(R,S)-(4-chlorophenyl)-2-oxo-1,3,2-dioxaphosphorinan-2-yl]uridine;
4'-azido-cis-5'-O-[4-(R,S)-(4-bromophenyl)-2-oxo-1,3,2-dioxaphosphorinan-2-yl]uridine;
4'-azido-cis-5'-O-[4-(R,S)-(2-bromophenyl)-2-oxo-1,3,2-dioxaphosphorinan-2-yl]uridine;
4'-azido-cis-5'-O-[4-(R,S)-(2-chlorophenyl)-2-oxo-1,3,2-dioxaphosphorinan-2-yl]uridine;
4'-azido-cis-5'-O-[4-(R,S)-(3-bromo-5-fluorophenyl)-2-oxo-1,3,2-dioxaphosphorinan-2-yl]uridine;
4'-azido-cis-5'-O-[4-(R,S)-(2,4-dichlorophenyl)-2-oxo-1,3,2-dioxaphosphorinan-2-yl]uridine;
4'-azido-cis-5'-O-[4-(R,S)-(2-chloro-6-fluorophenyl)-2-oxo-1,3,2-dioxaphosphorinan-2-yl]uridine;
4'-azido-cis-5'-O-[4-(R,S)-(2,5-dichlorophenyl)-2-oxo-1,3,2-dioxaphosphorinan-2-yl]uridine;
4'-azido-cis-5'-O-[4-(R,S)-(2,4-difluorophenyl)-2-oxo-1,3,2-dioxaphosphorinan-2-yl]uridine;
4'-azido-cis-5'-O-[4-(R,S)-(3-bromo-6-fluorophenyl)-2-oxo-1,3,2-dioxaphosphorinan-2-yl]uridine;
4'-azido-cis-5'-O-[4-(R,S)-(2-chloro-4-fluorophenyl)-2-oxo-1,3,2-dioxaphosphorinan-2-yl]uridine;
4'-azido-cis-5'-O-[4-(R,S)-(2,3-difluorophenyl)-2-oxo-1,3,2-dioxaphosphorinan-2-yl]uridine;
4'-azido-cis-5'-O-{4-(R,S)-[3,5-di-(trifluoromethyl)phenyl]-2-oxo-1,3,2-dioxaphosphorinan-2-yl}uridine;
4'-azido-cis-5'-O-[4-(R,S)-(3-trifluoromethylphenyl)-2-oxo-1,3,2-dioxaphosphorinan-2-yl]uridine;
4'-azido-cis-5'-O-[4-(R,S)-(2-trifluoromethylphenyl)-2-oxo-1,3,2-dioxaphosphorinan-2-yl]uridine;
4'-azido-cis-5'-O-[4-(R,S)-(3-cyanophenyl)-2-oxo-1,3,2-dioxaphosphorinan-2-yl]uridine;
4'-azido-cis-5'-O-[4-(R,S)-(4-trifluoromethylphenyl)-2-oxo-1,3,2-dioxaphosphorinan-2-yl]uridine;
4'-azido-cis-5'-O-[4-(R,S)-(3,5-dichlorophenyl)-2-oxo-1,3,2-dioxaphosphorinan-2-yl]uridine;
4'-azido-cis-5'-O-[4-(S)-(3,5-difluorophenyl)-2-oxo-1,3,2-dioxaphosphorinan-2-yl]uridine;
4'-azido-cis-5'-O-[4-(S)-(pyrid-4-yl)-2-oxo-1,3,2-dioxaphosphorinan-2-yl]uridine, hydrochloride salt;

4'-azido-cis-5'-O-[4-(R,S)-(3,4-dichlorophenyl)-2-oxo-1,3,2-dioxaphosphorinan-2-yl]uridine;
4'-azido-cis-5'-O-[4-(R,S)-(pyrid-3-yl)-2-oxo-1,3,2-dioxaphosphorinan-2-yl]uridine, hydrochloride salt 4'-azido-cis-5'-O-[4-(R,S)-(3-bromopyrid-5-yl)-2-oxo-1,3,2-dioxaphosphorinan-2-yl]uridine, hydrochloride salt 4'-azido-cis-5'-O-[4-(R,S)-(2-fluorophenyl)-2-oxo-1,3,2-dioxaphosphorinan-2-yl]uridine;
4'-azido-cis-5'-O-[4-(R,S)-(2,6-difluorophenyl)-2-oxo-1,3,2-dioxaphosphorinan-2-yl]uridine;
4'-azido-cis-5'-O-[4-(R,S)-(2,6-dichlorophenyl)-2-oxo-1,3,2-dioxaphosphorinan-2-yl]uridine;
4'-azido-cis-5'-O-[4-(R,S)-(2-fluoro-4-chlorophenyl)-2-oxo-1,3,2-dioxaphosphorinan-2-yl]uridine 4'-azido-cis-5'-O-[4-(R,S)-(2-fluoro-4-bromophenyl)-2-oxo-1,3,2-dioxaphosphorinan-2-yl]uridine;
2'3'-O-(3-methylbutanoyl)-4'-azido-cis-5'-O-[4-(R,S)-(3-cyanophenyl)-2-oxo-1,3,2-dioxaphosphorinan-2-yl]uridine
4'-azido-cis-5'-O-[4-(S)-(3-chlorophenyl)-2-oxo-1,3,2-dioxaphosphorinan-2-yl]uridine 2',3'-O-bis-propionate;
4'-azido-cis-5'-O-[4-(S)-(3-chlorophenyl)-2-oxo-1,3,2-dioxaphosphorinan-2-yl]-2',3'-O-bis -pivaloyl-uridine;
4'-azido-cis-5'-O-[4-(S)-(3-chlorophenyl)-2-oxo-1 ,3,2-dioxaphosphorinan-2-yl]-2',3'-O-bis -pentanoyl-uridine;
2',3'-O-(3-methylbutanoyl)-4'-azido-cis-5'-O-[4-(S)-(3-chlorophenyl)-2-oxo-1,3,2-dioxaphosphorinan-2-yl]uridine;
2',3'-O-bis-isobutanoyl-4'-azido-cis-5'-O-[4-(S)-(3-chlorophenyl)-2-oxo-1,3,2-dioxaphosphorinan-2-yl]uridine;
2',3'-O-bis-n-butanoyl-4'-azido-cis-5'-O-[4-(S)-(3-chlorophenyl)-2-oxo-1,3,2-dioxaphosphorinan-2-yl]uridine;
4'-azido-cis-5'-O-[4-(S)-(3-chlorophenyl)-2-oxo-1 ,3,2-dioxaphosphorinan-2-yl]-2',3'-O-bis -(cyclopropylcarbonyl)uridine;
4'-azido-cis-5'-O-[4-(S)-(3-chlorophenyl)-2-oxo-1 ,3,2-dioxaphosphorinan-2-yl]-2',3'-O-bis -(2-cyclopropylacetyl)-uridine;
2',3'-O-bis-(oxazole-4-carbonyl)-4'-azido-cis-5'-o-[4-(S)-(3-chlorophenyl)-2-oxo-1,3,2-dioxaphosphorinan-2-yl]uridine;
2',3'-O-bis-(furan-3-carbonyl)-4'-azido-cis-5'-o-[4-(S)-(3-chlorophenyl) -2-oxo-1,3,2 -dioxaphosphorinan-2-yl]uridine;
4'-azido-cis-5'-O-[4-(S)-(3-chlorophenyl)-2-oxo-1,3,2-dioxaphosphorinan-2-yl]-2',3'-O-bis -(2-ethoxyacetyl)-uridine;
4'-azido-cis-5'-O-[4-(S)-(3-chlorophenyl)-2-oxo-1,3 ,2-dioxaphosphorinan-2-yl]-2',3'-O-bis -(2-methoxyacetyl)-uridine;
4'-azido-cis-5'-O-[4-(S)-(3-chlorophenyl)-2-oxo-1,3,2-dioxaphosphorinan-2-yl]uridine 2',3'-O-bis-(ethoxycarbonate);
4'-azido-cis-5'-O-[4-(S)-(3-chlorophenyl)-2-oxo-1,3,2-dioxaphosphorinan-2-yl]uridine 2',3'-O-bis-(isopropoxycarbonate);

4'-Azido-cis-5'-O-[4-(S)-(3-chlorophenyl)-2-oxo-1,3,2-dioxaphosphorinan-2-yl]-2',3'-O-bis-(pyrrole-2-carboxyl)uridine;
4'-Azido-cis-5'-O-[4-(S)-(3-chlorophenyl)-2-oxo-1,3,2-dioxaphosphorinan-2-yl]-2',3'-O-bis-(pyrazol-5-carboxyl)-uridine;
4'-Azido-cis-5'-O-[4-(S)-(3-chlorophenyl)-2-oxo-1,3,2-dioxaphosphorinan-2-yl]-2',3'-O-bis -(pyridine-3-carboxyl)-uridine;
4'-Azido-cis-5'-O-[4-(S)-(3-chlorophenyl)-2-oxo-1,3,2-dioxaphosphorinan-2-yl]-2',3'-O-bis-(2-ethoxyacetyl)-uridine;
4'-Azido-cis-5'-O-[4-(S)-(3-chlorophenyl)-2-oxo-1,3,2-dioxaphosphorinan-2-yl]-2',3'-O-bis-(2-methoxyacetyl)-uridine;
4'-Azido-cis-5'-O-[4-(S)-(3-chlorophenyl)-2-oxo-1,3,2-dioxaphosphorinan-2-yl]uridine 2',3'-O-bis-(ethoxycarbonate);
4'-Azido-cis-5'-O-[4-(S)-(3-chlorophenyl)-2-oxo-1,3,2-dioxaphosphorinan-2-yl]uridine 2',3'-O-bis-(isopropoxycarbonate); and,
and stereoisomers thereof.

11. A compound according to claim 1 which compound is:
4'-Azido-cis-5'-O-[4-(S)-(3-chlorophenyl)-2-oxo-1,3 ,2-dioxaphosphorinan-2-yl]uridine 2',3'-O-bis-propionate, 4'-azido-cis-5'-O-[4-(S)-(3-chlorophenyl)-2-oxo-1,3 ,2-dioxaphosphorinan-2-yl]uridine 2',3'-O-bis-valeroate, 4'-azido-cis-5'-O-[4-(S)-(3-chlorophenyl)-2-oxo-1,3 ,2-dioxaphosphorinan-2-yl]uridine 2',3'-O-bis-isovaleroate.

12. A method for treating a disease caused by the Hepatitis C Virus (HCV) virus comprising administering to a patient in need thereof, a therapeutically effective quantity of a compound according to claim 1.

13. The method of claim 12 further co-comprising administering at least one immune system modulator and/or at least one antiviral agent that inhibits replication of HCV.

14. The method of claim 13 wherein the immune system modulator is an interferon, interleukin, tumor necrosis factor or colony stimulating factor.

15. The method of claim 14 wherein the immune system modulator is an interferon or chemically derivatized interferon.

16. The method of claim 13 wherein the antiviral compound is selected from the group consisting of a HCV protease inhibitor, another HCV polymerase inhibitor, a HCV helicase inhibitor, a HCV primase inhibitor and a HCV fusion inhibitor.

17. A method of inhibiting replication in HCV comprising administering a therapeutically effective quantity of a compound according to claim 1.

18. A pharmaceutical composition comprising a therapeutically effective quantity of a compound according to claim 1 admixed with at least one pharmaceutically acceptable carrier, diluent or excipient.

* * * * *